US009574012B2

(12) United States Patent
Li et al.

(10) Patent No.: US 9,574,012 B2
(45) Date of Patent: Feb. 21, 2017

(54) AGR2 BLOCKING ANTIBODY AND USE THEREOF

(75) Inventors: Dawei Li, Shanghai (CN); Zhenghua Wu, Shanghai (CN); Hao Guo, Shanghai (CN); Qi Zhu, Shanghai (CN); Dhahiri S. Mashausi, Shanghai (CN)

(73) Assignees: Sanofi (China) Investment Co., Ltd. Shanghai Branch, Shanghai (CN); Shanghai Jiao Tong University, Shanghai (CN)

( * ) Notice: Subject to any disclaimer, the term of this patent is extended or adjusted under 35 U.S.C. 154(b) by 158 days.

(21) Appl. No.: 14/130,767

(22) PCT Filed: Jul. 5, 2012

(86) PCT No.: PCT/CN2012/000926
§ 371 (c)(1),
(2), (4) Date: Jul. 25, 2014

(87) PCT Pub. No.: WO2013/004076

PCT Pub. Date: Jan. 10, 2013

(65) Prior Publication Data
US 2014/0328829 A1    Nov. 6, 2014

(30) Foreign Application Priority Data
Jul. 5, 2011  (CN) .......................... 2011 1 0186469

(51) Int. Cl.
*C07K 16/40*  (2006.01)
*A61K 39/395*  (2006.01)
*C12P 21/08*  (2006.01)
*A61K 45/06*  (2006.01)
*C07K 16/22*  (2006.01)
*A61K 39/00*  (2006.01)

(52) U.S. Cl.
CPC .......... *C07K 16/40* (2013.01); *A61K 39/3955* (2013.01); *A61K 45/06* (2013.01); *C07K 16/22* (2013.01); *A61K 2039/505* (2013.01); *C07K 2317/24* (2013.01); *C07K 2317/34* (2013.01); *C07K 2317/73* (2013.01); *C12N 2510/02* (2013.01)

(58) Field of Classification Search
None
See application file for complete search history.

(56) References Cited

U.S. PATENT DOCUMENTS

| 4,816,567 A | 3/1989 | Cabilly et al. | |
|---|---|---|---|
| 2003/0105000 A1* | 6/2003 | Pero ...................... | A61K 38/06 514/19.3 |
| 2004/0180002 A1* | 9/2004 | Young .................... | C07K 16/00 424/1.49 |
| 2004/0197328 A1* | 10/2004 | Young .............. | A61K 47/48569 424/141.1 |

FOREIGN PATENT DOCUMENTS

| CN | 101519649 A | 9/2009 | |
|---|---|---|---|
| CN | 102268089 A | 12/2011 | |
| EP | 2 520 588 A1 | 11/2012 | |
| KR | 20100031190 A | 3/2010 | |
| RU | 2008110494 A | 9/2009 | |
| WO | WO2004/031239 | 4/2004 | |
| WO | WO 2007/141280 A2 * | 12/2007 | ........... G01N 33/574 |
| WO | WO2008/025964 | 3/2008 | |
| WO | WO 2013/059885 | 5/2013 | |

OTHER PUBLICATIONS

Li et al. (Proceedings: AACR 103rd Annual Meeting Mar. 31, 2012-Apr. 4, 2012, Cancer Res 2012; 72(8 Suppl), Ab#: 4638).*
Kaiser (Science, 2006, 313: 1370).*
Gura (Science, 1997, 278:1041-1042).*
Ibragimova and Wade (Biophysical Journal, Oct. 1999, vol. 77, pp. 2191-2198).*
Burgess et al. (J of Cell Bio. 111:2129-2138, 1990).*
Coleman et al. (Research in Immunology, 1994; 145(1): 33-36).*
Rudikoff et al. (PNAS USA, 1982, 79: 1979-1983).*
Zheng et al. "Oncogenic Role of Agr2 in Esophageal Adenocarcinoma" AGA Abstracts, p. A-636.
European Application No. 12807760.9, extended European search report dated Feb. 3, 2015, 4 pages.
Van Der Bij, G.J., et al., Experimentally induced liver metastases from colorectal cancer can be prevented by mononuclear phagocyte-mediated monoclonal antibody therapy. J Hepatol., 2010, 53(4) p. 677-85.
Bhuvaneswari, R., et al., Targeting EGFR with photodynamic therapy in combination with Erbitux enhances in vivo bladder tumor response. Mol Cancer, 2010, 8 :94, 11 pages.
Khalili, P., et al., Effect of Herceptin on the development and progression of skeletal metastases in a xenograft model of human breast cancer. Oncogene, 2005. 24(44) p. 6657-66.
Jerome, L., et al., Recombinant human insulin-like growth factor binding protein 3 inhibits growth of human epidermal growth factor receptor-2-overexpressing breast tumors and potentiates herceptin activity in vivo. Cancer Res, 2006. 66(14) p. 7245-52.
Guan, H., et al., Herceptin down-regulates HER-2/neu and vascular endothelial growth factor expression and enhances taxol-induced cytotoxicity of human Ewing's sarcoma cells in vitro and in vivo. Clin Cancer Res, Mar. 1, 2005, 11(5) p. 2008-17.
Kuang, W.W., et al., Differential screening and suppression subtractive hybridization identified genes differentially expressed in an estrogen receptor-positive breast carcinoma cell line, Nucleic Acids Res, 1998, 26(4) p. 1116-23.

(Continued)

*Primary Examiner* — Peter J Reddig
(74) *Attorney, Agent, or Firm* — Lathrop & Gage LLP; James H. Velema, Esq.

(57) ABSTRACT

Disclosed is an AGR2 blocking monoclonal antibody, and in particular, a humanized monoclonal antibody for blocking AGR2. Also disclosed is a pharmaceutical composition containing the antibody and a method for preparing the same, and a use of the antibody in blocking tumor growth and metastasis.

17 Claims, 13 Drawing Sheets

(56) References Cited

OTHER PUBLICATIONS

Thompson, D.A. and R.J. Weigel hAG-2, the Human Homologue of the *Xenopus laevis* Cement Gland Gene XAG-2, Is Coexpressed with Estrogen Receptor in Breast Cancer Cell Lines Biochem Biophys Res Commun, 1998, 251(1) p. 111-116.
Persson, S., et al. Diversity of the protein disulfide isomerase family: Identification of breast tumor induced Hag2 and Hag3 as novel members of the protein family, Mol. Phylogenet. Evol. 2005 36(3) p. 734-40.
Park, S.W., et al., The protein disulfide isomerase AGR2 is essential for production of intestinal mucus, PNAS, Apr. 28, 2009, 106(17) p. 6950-5.
Anelli, T., et al., ERp44, a novel endoplasmic reticulum folding assistant of the thioredoxin family, EMBO J, 2002. 21(4) p. 835-44.
Anelli, T., et al., Thiol-mediated protein retention in the endoplasmic reticulum: the role of ERp44, EMBO J, 2003. 22(19) p. 5015-22.
Liu D., et al. Human Homologue of Cement Gland Protein, a Novel Metastasis Inducer Associated with Breast Carcinomas Cancer Res., May 1, 2005, 65(9) 3796-3805.
Ramachandran, V., et al. Anterior Gradient 2 Is Expressed and Secreted during the Development of Pancreatic Cancer and Promotes Cancer Cell Survival Cancer Res, Oct. 1, 2008, 68(19) 7811-7818.
Zhang Y, et al., ErbB3 Binding Protein 1 Represses Metastasis-Promoting Gene Anterior Gradient Protein 2 in Prostate Cancer, Cancer Res, Jan. 1, 2010, 70(1) 240-248.
Vanderlaag, K. E., et al., Anterior gradient-2 plays a critical role in breast cancer cell growth and survival by modulating cyclin D1, estrogen receptor-α and surviving, Breast Cancer Research, 2010, 12:R32, 15 pages.
Tonini, T. et al., Molecular basis of antiogenesis and cancer, Oncogene, 22, 6549-6556 (2003).
Sato, Y., Molecular diagnosis of tumor angiogenesis and anti-angiogenic cancer therapy, Int. J. Clin. Oncol., 8 200-206 (2003).
Jones, P.T., et al., Replacing the complementarity-determining regions in human antibody with those from a mouse, Nature, 321 522-525 (May 29, 1986).
Riechmann, L., et al., Reshaping human antibodies for therapy, Nature 332 323-327(Mar. 24, 1988).
Verhoeyen M., et al., Reshaping Human Antibodies; Grafting an Antilysozyme Activity, Science, 239 1534-1536 (1988).
Sims et al., A humanized CD18 antibody can block function without cell destruction, J. Immunol., 151 2296-2308 (Aug. 15, 1993).
Chothia et al., Canonical Structures for the Hypervariable Regions of Immunoglobulins, J. Mol. Biol., 196 901-917 (1987).
Carter et al., Humanization of an anti-p185HER2 antibody for human cancer therapy, Proc. Natl. Acad. Sci. USA, 89 4285-4289, (May 1992).
Presta et al., Humanization of an antibody directed against IgE, J. Immunol., (Sep. 1993) 151 2623-2632.
Marks, J. D. et al., By-passing Immunization, Human Antibodies from V-gene Libraries Displayed on Phage, J. Mol. Biol., 222 581-597, 1991.
Wu, Z. H. et al. Preparation, characterization and potential application of monoclonal antibody against AGR2, Chinese Journal of Cellular and Molecular Immunology, vol. 26, No. 1, Jan. 2010, pp. 49-51.
PCT/CN2012/000926 International Preliminary Report on Patentability, English Translation, Chapter II demand received: May 6, 2013, 10 pages.
PCTCN2012000926 International Search Report, mailed Oct. 18, 2012, English Translation, 5 pages.
European Application No. 12807760.9, Communication pursuant to Article 94(3) EPC dated Sep. 29, 2015, 4 pages.
Harding, F.A. et al: "The immunogenicity of humanized and fully human antibodies: Residual immunogenicity resides in the CDR regions", Mabs, Landes Bioscience, US, vol. 2, No. 3, May 1, 2010 (May 1, 2010), pp. 256-265.
Tsurushita N, et al. "Design of humanized antibodies: From anti-Tac to Zenapax", Methods, Academic Press, vol. 36, No. 1, May 1, 2005 (May 1, 2005), pp. 69-83.
Wake et al. (Aug. 2009) "Antibody Medicine," Journal of Okayama Medical Association. 121:119-122.—with English translation.
Notice of Rejection corresponding to Japanese Patent Application No. 2014-517400, dated Apr. 26, 2016.—with English translation.
Office Action corresponding to European Patent Application No. 12807760.9, dated Apr. 29, 2016.
Office Action corresponding to Australian Patent Application No. 2012278751, issued Jul. 21, 2016.
Office Action corresponding to Russian Patent Application No. 2014103784, received Jul. 18, 2016-with English translation.
Notice of Allowance corresponding to Russian Patent Application No. 2014103784, issued Oct. 27, 2016-with English translation.
Office Action corresponding to Israeli Patent Application No. 230227, issued Nov. 29, 2016-with English summary.
Office Action corresponding to Mexican Patent Application No. Mx/a/2014/000260, issued Nov. 29, 2016-with English summary.

\* cited by examiner

Figure 1: Detection of AGR2 specificity by ELISA
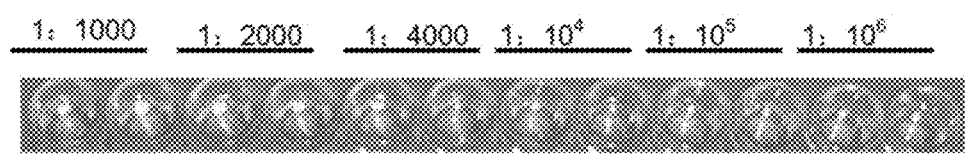
Figure 2: Detection of AGR2 specificity by immunoblotting
A
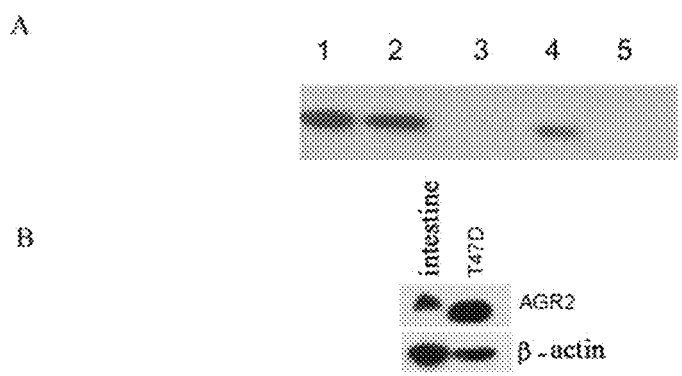
B
Figure 3: Detection of AGR2 specificity by immunoprecipitation
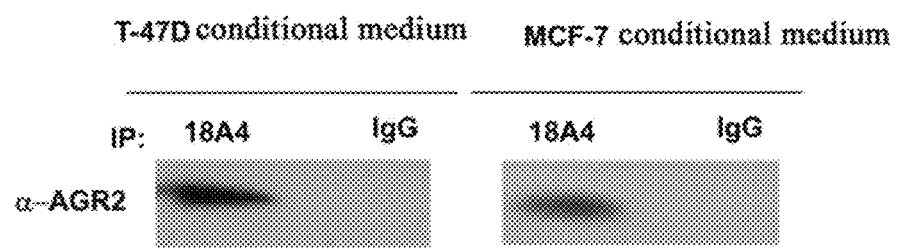

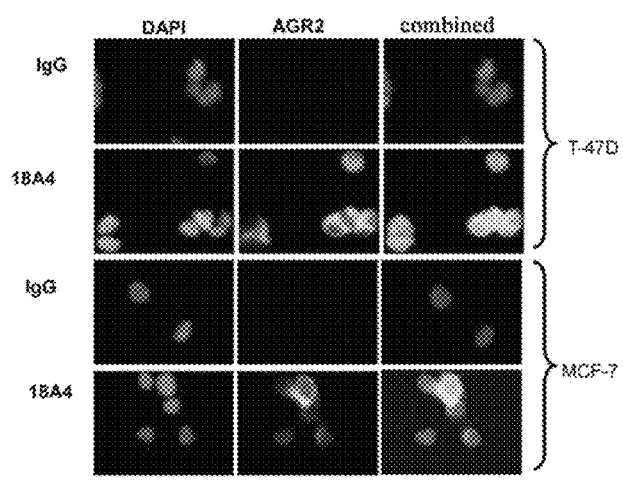
Figure 4: Detection of AGR2 specificity by immunofluorescence
Figure 5A: Alignment of the light chain variable regions between the murine monoclonal antibody 18A4 and 18A4HU1
Figure 5B: Alignment of the heavy chain variable regions between the murine monoclonal antibody 18A4 and 18A4HU1

Figure 6A: Structural comparison between the light chain variable region (V$_L$) of the murine monoclonal antibody 18A4 and the V$_L$ of the humanized 18A4HU1 version

|  | FR1 | CDR1 | FR2 | CDR2 |
|---|---|---|---|---|
| 18A4/L | DIVLTQSPASLTVSLGQRATISC | RASKSVSTSGYSYMH | WYQRKPGQPPKLLIY | LASNLES |
| IGKV3-20*02 | E---------T-SL-P-E----L-- | ------Q---S-***-LA | ------Q------A-R----- | GASSRAT |
| IGKV3 (consensus sequence) | E--------*T-SL-P-E----L-- | *********- | ------Q------A-R----* | ******* |
| 18A4HU1/L | E---------T-SL-P-E----L-- |  | ------Q------A-R----- |  |

|  | FR3 | CDR3 | FR4 |
|---|---|---|---|
| 18A4/L | GVPARFSGSGSGTDFTLNIHPVEGEDAATYYC | QHIRELPRT | FGGGTKLEIK |
| IGKV3-20*02 | --I-------------------T-SRL-P---F------ | -*****Q- | ---Q----V----- |
| IGKV3(consensus sequence) | --I-*-----------------T-SRL-P---F------ | ******** | ---*----*----- |
| 18A4HU1/L | --I-------------------T-SRL-P---F------ |  |  |

Figure 6B: Structural comparison between the heavy chain variable region (V$_H$) of the murine monoclonal antibody 18A4 and the V$_H$ of the humanized 18A4U1 version

|  | FR1 | CDR1 | FR2 | CDR2 |
|---|---|---|---|---|
| 18A4/H | EVQLQQPGAELVKPGASVKISCKASAYTFT | DYNMD | WVKQSHGKSLEWIG | DINPNYDTTSYNQKFKG |
| IGHV1-46*03 | Q-----V-S-----VK---------V----G----- | S-Y-H | ---R-AP-QG-----M-- | I----SGGS----A----Q- |
| IGHV1 (consensus sequence) | Q-----V-S-----VK--*------V----G----- | ***** | ---R-AP-QG----- | ******************* |
| 18A4HU1/H | Q-----V-S-----VK---------V----G----- |  | ---R-AP-QG----- |  |

|  | FR3 | CDR3 | FR4 |
|---|---|---|---|
| 18A4/H | KATLTVDKSSSTAYMELRSLTSEDIAVYYCAR | SNSGYSSPRDY | WGQGTSVTVSS |
| IGHV1-46*03 | NV-N-R-T-T--V------S--R | ***Y**FDY | ------L----- |
| IGHV1 (consensus sequence) | ***-*-*-*-T*-*------S--R | ********** | ------L----- |
| 18A4HU1/H | ----------------T------S--R | ----------- | ------L----- |

Figure 7: Diagram for the construction of the plasmid for expressing the intact antibody
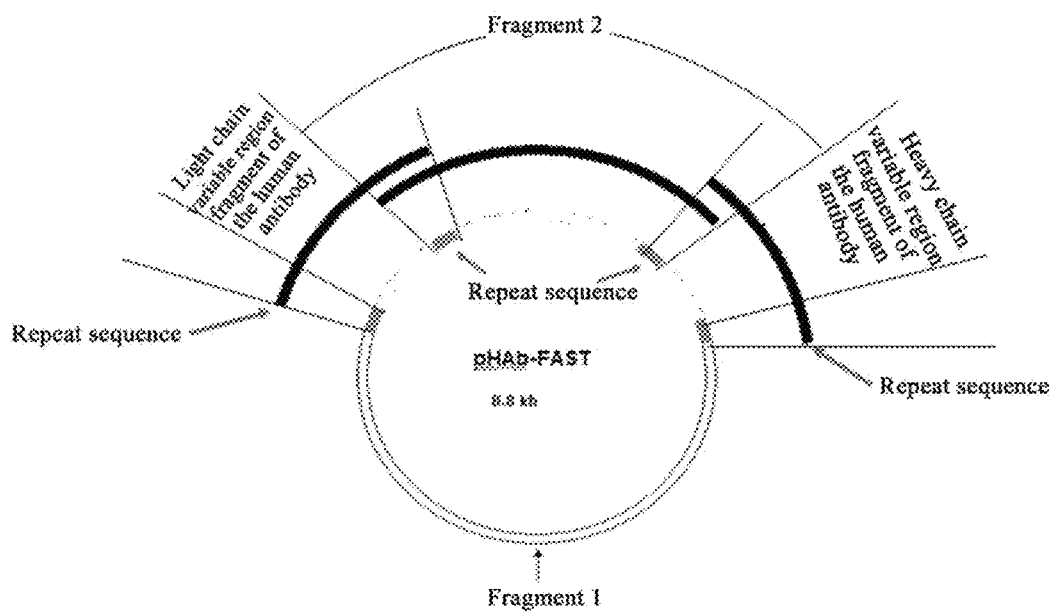
Figure 8: SDS-PAGE electrophoresis of the purified antibody
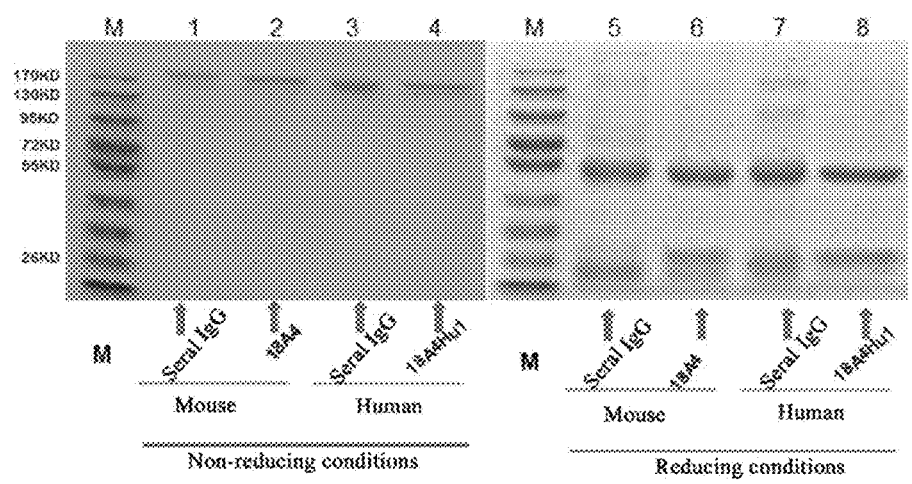

Figure 9: Experimental results for the antibody affinity assayed by a competitive ELISA

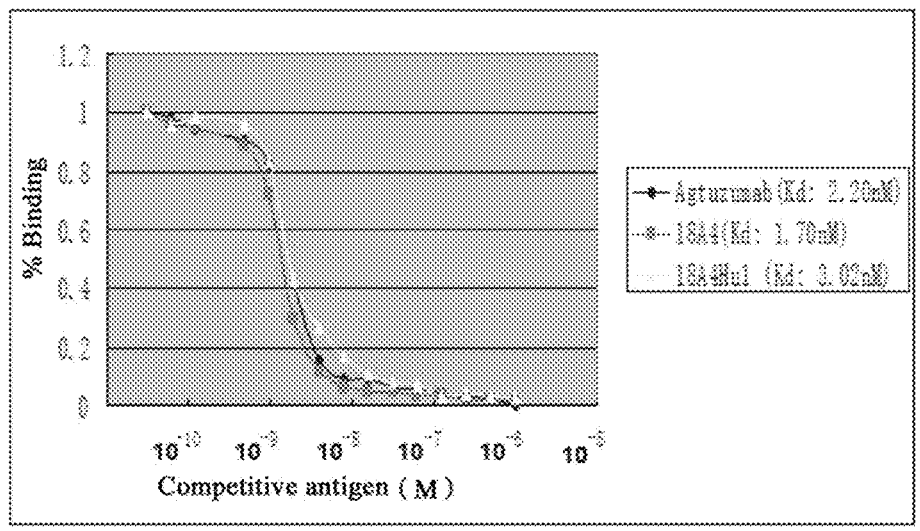

Figure 10: Alignment of the mutated positions in the humanized antibody variant and the change of the number of the potential T cell epitopes Heavy chain mutation

| Name | Mutation | HCDR2 and HFR2 T cell epitopes | Total T cell epitopes |
|---|---|---|---|
| 18A4 | YNQKFKGKATLTV | 5+11 | 60 |
| 18A4Hu1 | YNQKFKGKATLTV | 5+11 | 44 |
| 18A4Hu2 | YNQKFKGKVTMTV | 2+6 | 36 |
| 18A4Hu3 | YNQKFKGRVTMTV | 2+5 | 35 |
| Agtuzumab | YNQKFQGRVTMTV | 0+5 | 33 |

Light chain mutation

| Name | Mutation | LFR2 and LCDR2 T cell epitopes | Total T cell epitopes |
|---|---|---|---|
| 18A4 | LLIYLASNLES | 5+3+14 | 41 |
| 18A4Hu1 | LLIYLASNLES | 5+3+14 | 26 |
| 18A4Hu4 | LLIYLASSLET | 5+2+1 | 12 |
| 18A4Hu5 | LLIYLASSRET | 2+2+1 | 9 |

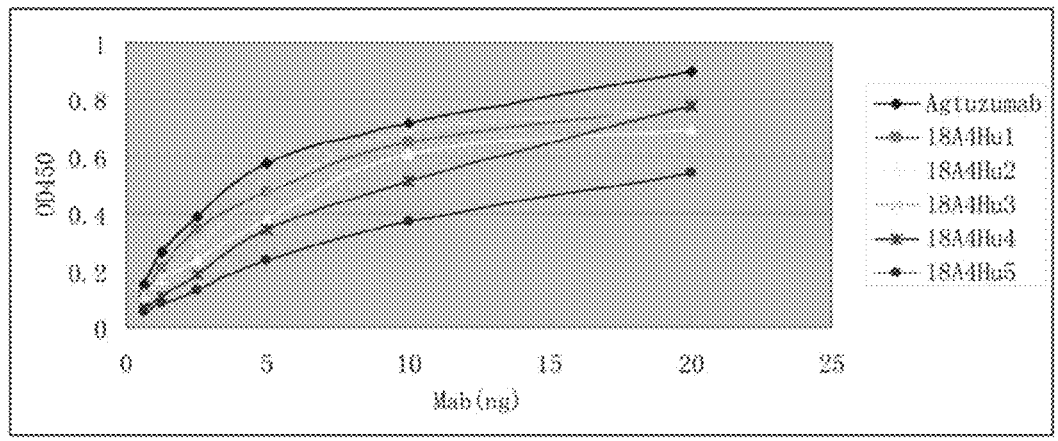
Figure 11: Antigen binding curve of the humanized antibody variants
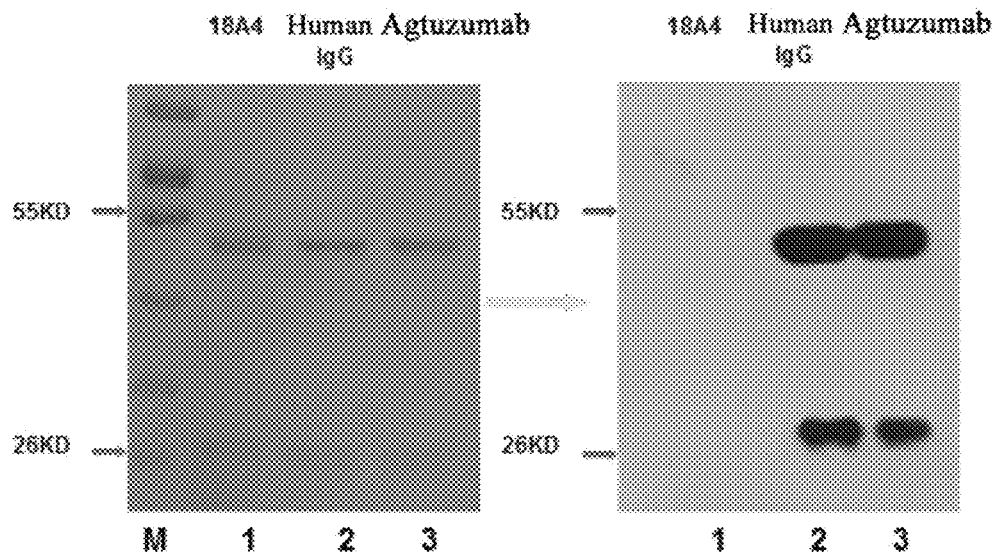
Figure 12: Identification of the species specificity of the humanized antibody Agtuzumab by western blot Figure 13: Detection of the antigen binding specificity of the humanized antibody Agtuzumab by western blot
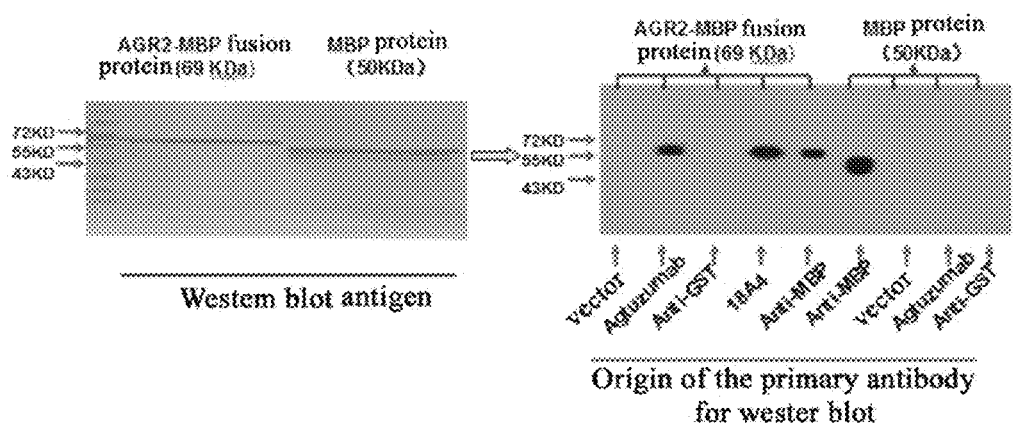
Figure 14: Detection of the binding specificity of the humanized antibody Agtuzumab to the antigens in the cell lysate by western blot
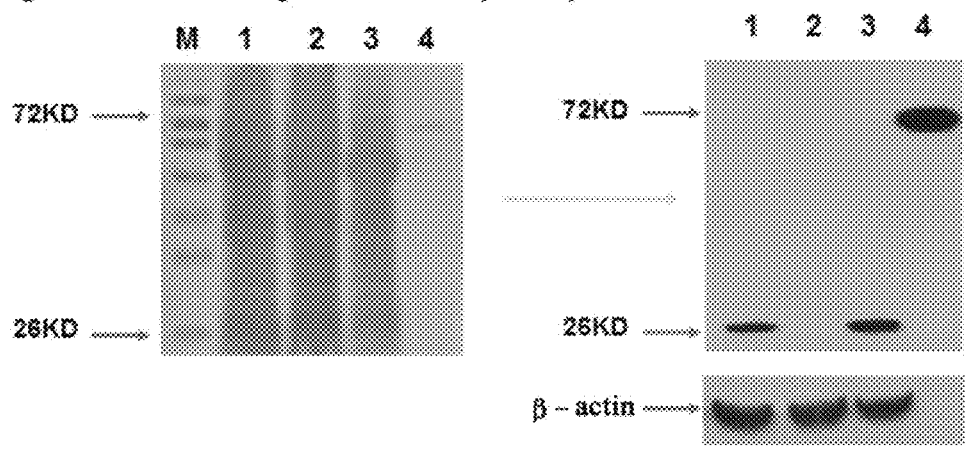

Figure 15: Detection of the ability of the humanized antibody Agtuzumab to bind to the natural AGR in the MCF7 cells by immunoprecipitation (IP)
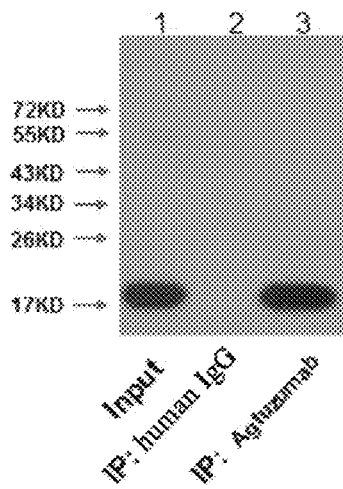
Figure 16: AGR2-MBP mutants generated by mutations according to the analysis of potential epitopes of AGR2
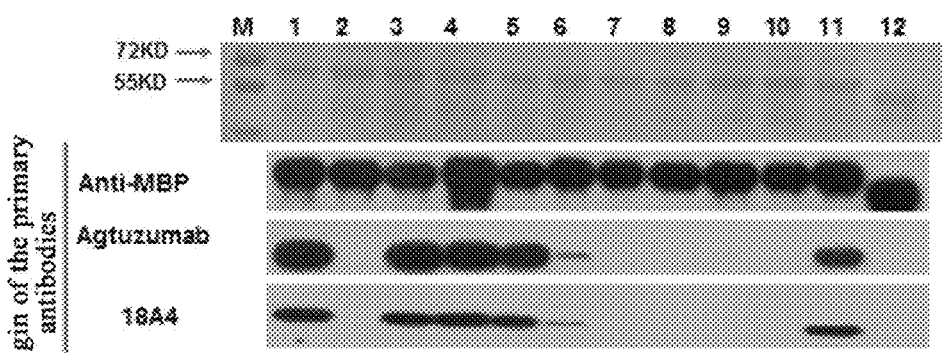
Figure 17: Binding of the murine 18A4 and the humanized antibody Agtuzumab to the AGR2-MBP mutants

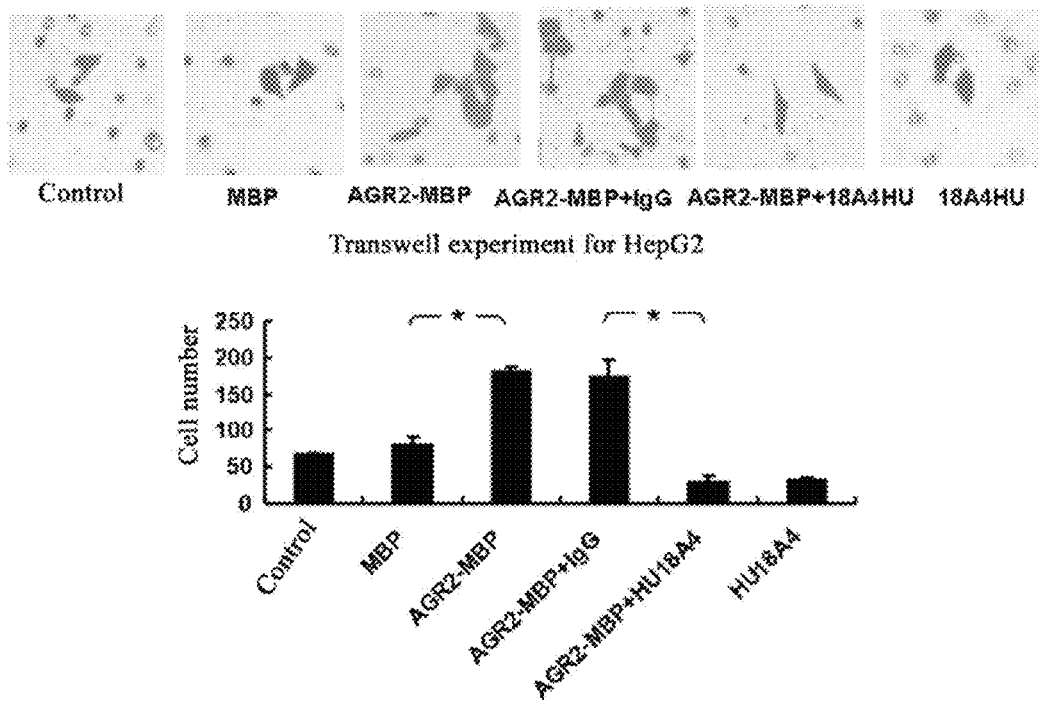
Figure 18: Detection of the ability of antibodies to inhibit the invasive metastasis of the liver cancer cell HepG2 in vitro by transwell experiments.
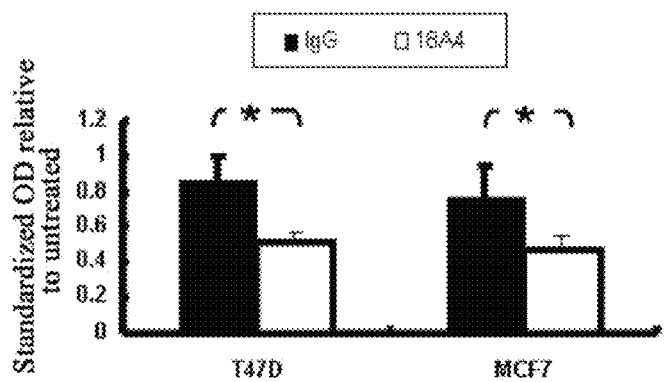
Figure 19: Detection of the ability of antibodies to inhibit the growth and migration of the breast cancer cells T47D and MCF 7 in vitro by MTT.

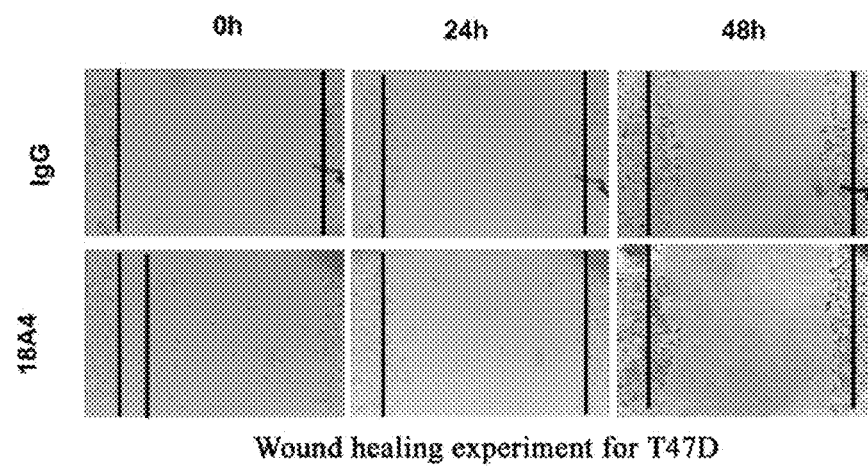
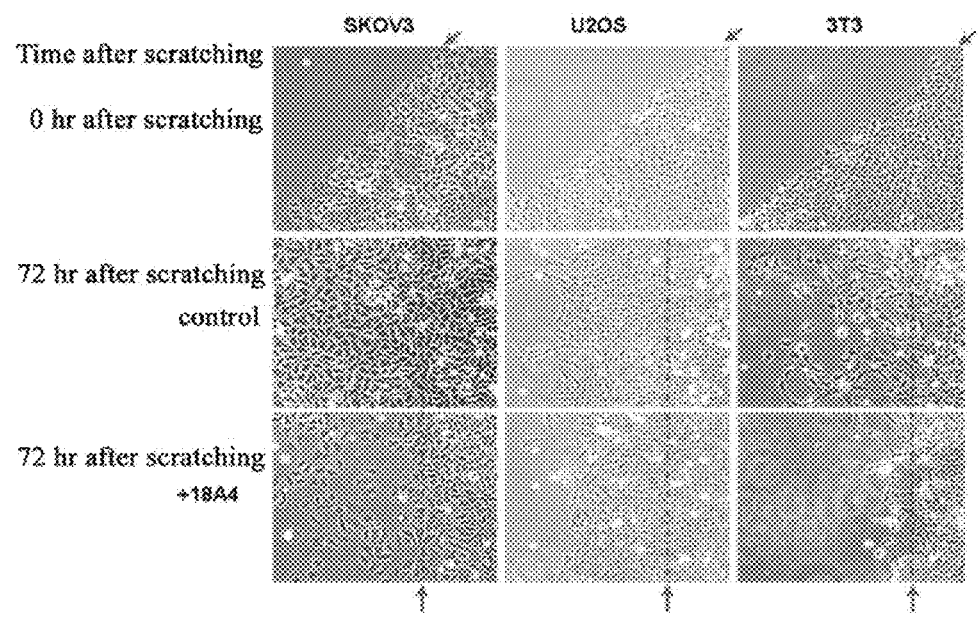
Figure 20: Detection of the ability of antibodies to inhibit the migration of the breast cancer cells T47D in vitro by wound healing assay.

Figure 21: Detection of the ability of antibodies to inhibit the invasive metastasis of the liver cancer cell HepG2 in vitro by transwell experiments
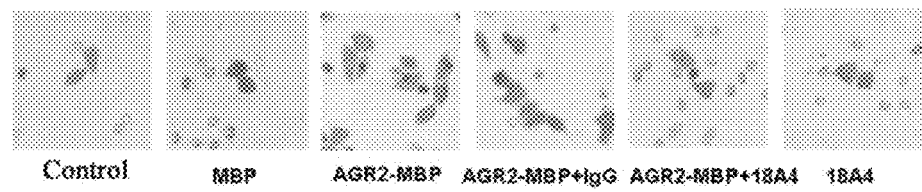
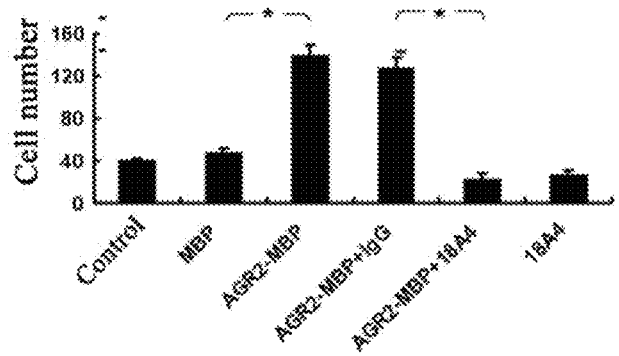
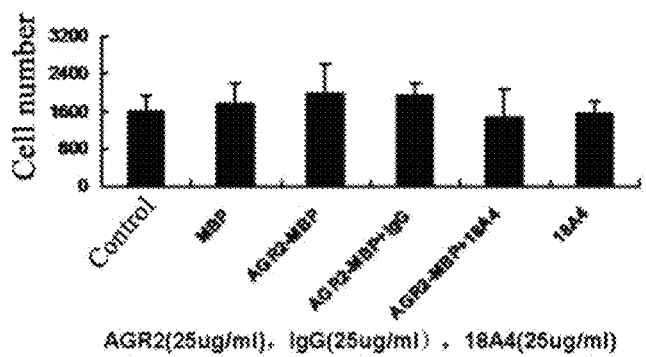

Figure 22: Detection of the ability of antibodies to inhibit the cell cycle of the breast cancer cells MCF-7 and T47D in vitro by cytometry

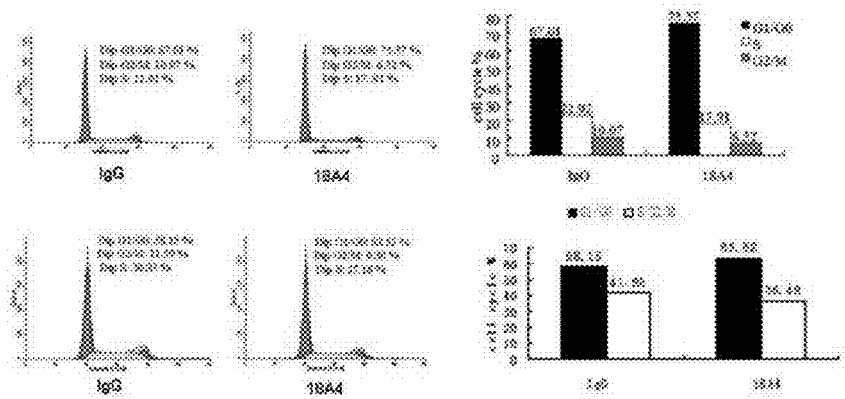

Figure 23: Confirmation of the binding of the antibodies to the AGR2 active site domain by western blot

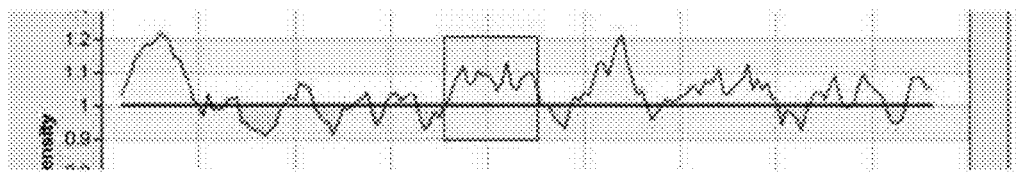

Figure 24: Confirmation of the binding of the antibodies to the AGR2 active site domain by western blot

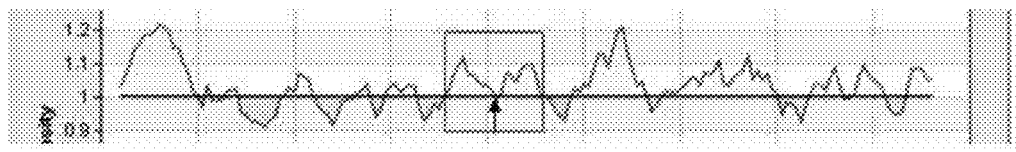

Figure 25: Confirmation of the binding of the antibodies to the AGR2 active site domain by western blot

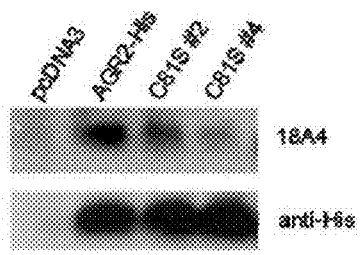

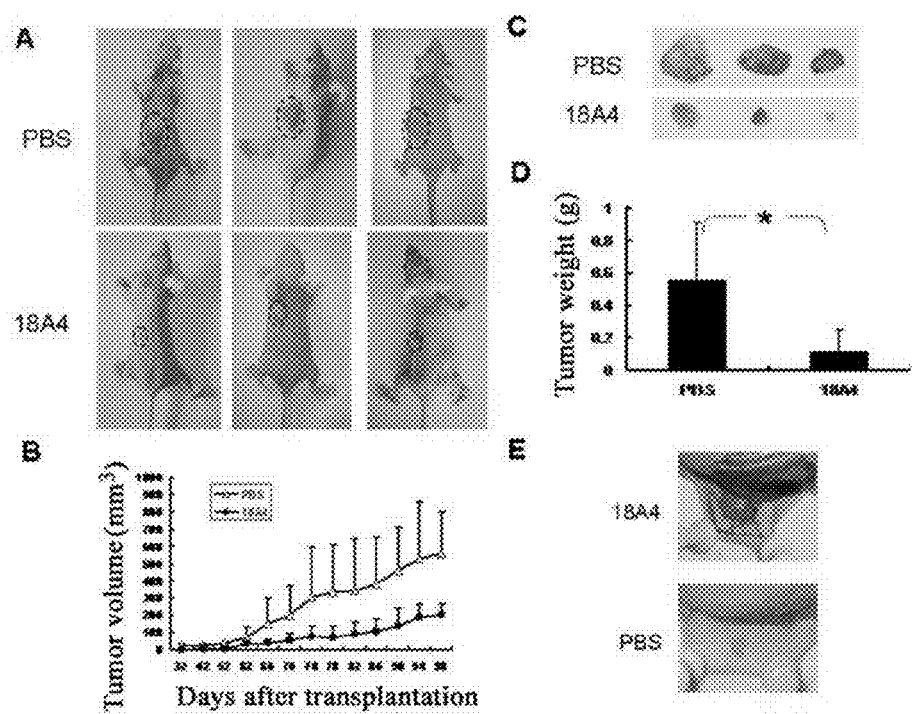
Figure 26: Tumor growth of animal

AGR2 BLOCKING ANTIBODY AND USE THEREOF

RELATED APPLICATIONS

This application claims the benefit of priority under 35 U.S.C. 371 of PCT application PCT/CN2012/000926 filed Jul. 5, 2012, which claims priority to Chinese patent application No. 201110186469.5 filed Jul. 5, 2011.

SEQUENCE LISTING

The instant application contains a Sequence Listing which has been submitted in ASCII format via EFS-Web and is hereby incorporated by reference in its entirety. The name of the Sequence Listing file is "553439 Substitute Sequence Listing Sep. 25 2016." It was created on Sep. 25, 2016 and the size of the file is 31.1 kilobytes.

FIELD OF INVENTION

The invention relates to a monoclonal antibody in the field of genetic immunology and molecular biological technology, in particular, to an AGR2 blocking antibody and use thereof.

BACKGROUND OF INVENTION

Anterior gradient-2 (AGR2) was first found by differential screening in a human breast cancer cell line with estrogen receptor expression (Kuang, W. W., et al., Nucleic Acids Res, 1998. 26(4): p. 1116-23), and subsequently, its full-length cDNA clone was obtained. After comparison, it was found to be homologous to a toad XA-2 development associated protein and was designated as hAG-2 (Thompson, D. A. and R. J. Weigel, hAG-2, Biochem Biophys Res Commun, 1998. 251(1): p. 111-6). AGR2 has a high homology with protein disulfide isomerase (PDI) (Persson, S., et al. Mol Phylogenet Evol 2005 36(3): p. 734-40), and has PDI activity (Park, S. W., et al., PNAS, 2009. 106(17): p. 6950-5). AGR2 has the PDI active site "CXXS", which is distinguished from the normal PDI site "CXXC". Through studies on other PDI proteins, it has been indicated that the "CXXS" active site has the function of disulfide bond rearrangement, but lacks the function of synthesizing the disulfide bond. That means that AGR2 has the function of disrupting the normal growth of cells but lacks the ability to recover their functions. (Anelli, T., et al., EMBO J, 2002. 21(4): p. 835-44. Anelli, T., et al., EMBO J, 2003. 22(19): p. 5015-22).

AGR2 is a marker protein for primary and secondary tumors, is detectable in the circular system of patients with a tumor, and is closely associated with the development and metastasis of tumors. AGR2 has the effect of promoting the transformation and migration of breast cancer cells (Liu D, et al. Cancer Res, 2005, 65(9): 3796-3805). AGR2 can increase the invasive ability of pancreatic cancer cells, thereby promoting the metastasis of the tumor (Ramachandran V, et al. Cancer Res, 2008, 68(19): 7811-7818). AGR2 plays a crucial role in the metastasis of prostate cancers (Zhang Y, et al. Cancer Res, 2010, 70(1): 240-248). It was not until 2010 that Kathryn et al. mentioned that AGR2 polyclonal antibody can inhibit the growth of breast cancer cells (Kathryn E Vanderlaag, et al. breast cancer, 2010, 12).

SUMMARY OF INVENTION

The invention relates to the following technical solutions:

An antibody specifically binding to AGR2 protein, which binds to essentially the same epitope of AGR2 protein as the murine anti-human AGR2 protein monoclonal antibody 18A4.

The antibody of Item 1, which is the murine anti-human monoclonal antibody 18A4 or humanized or chimeric form thereof.

The antibody of Item 1 or 2, wherein said epitope is located within the protein disulfide isomerase active domain of AGR2.

The antibody according to any one of Items 1 to 4, wherein the AGR2 active domain to which the antibody binds is CPHS (SEQ ID No. 14); preferably the antibody binds to the necessary binding region as shown by PLMII-HHLDE CPHSQALKKV FA (SEQ ID No. 15).

The antibody according to any one of the above Items comprising at least one sequence selected from the group consisting of
the heavy chain CDR1 amino acid sequence as shown in Seq ID No. 8, the heavy chain CDR2 amino acid sequence as shown in Seq ID No. 9, the heavy chain CDR3 amino acid sequence as shown in Seq ID No. 10, the light chain CDR1 amino acid sequence as shown in Seq ID No. 11, the light chain CDR2 amino acid sequence as shown in Seq ID No. 12, and the light chain CDR3 amino acid sequence as shown in Seq ID No. 13.

The antibody of Item 5 comprising the heavy chain CDR1 amino acid sequence as shown in DYNMD (Seq ID No. 8), the heavy chain CDR2 amino acid sequence as shown in DINPNYDTTSYNQKFQG (Seq ID No. 9), the heavy chain CDR3 amino acid sequence as shown in SM MGYGSP-MDY (Seq ID No. 10), the light chain CDR1 amino acid sequence as shown in RASKSVSTSGYSYMH (Seq ID No. 11), the light chain CDR2 amino acid sequence as shown in LASNLES (Seq ID No. 12), and the light chain CDR3 amino acid sequence as shown in QHIRELPRT (Seq ID No. 13).

The antibody of Item 6, wherein the heavy chain variable region amino acid sequence of the antibody is as shown in Seq ID No. 2, and the light chain variable region amino acid sequence of the antibody is as shown in Seq ID No. 1.

The antibody of Item 6, wherein the heavy chain variable region amino acid sequence of the antibody is as shown in Seq ID No. 4, and the light chain variable region amino acid sequence of the antibody is as shown in Seq ID No. 3.

The antibody according to any one of Items 1 to 8, which is a humanized antibody, preferably a humanized intact IgG1 antibody.

The antibody according to any one of Items 1 to 9, which is an antibody fragment, preferably an Fab, an Fab', an F(ab')$_2$, an Fv fragment, a linear antibody, or a single chain antibody, and more preferably an Fab fragment.

A pharmaceutical composition comprising the antibody according to any one of Items 1-10 and a pharmaceutically acceptable carrier.

An isolated nucleic acid encoding the antibody according to any one of Items 1 to 10.

A vector comprising the nucleic acid of Item 12.

A host cell comprising the vector of Item 13.

A method for producing a humanized antibody comprising cultivating the host cell of Item 14 so as to express the nucleic acid and produce the antibody.

The method of Item 15, further comprising recovering the antibody from the culture of the host cell.

A method for using the antibody according to any one of Items 1 to 10 for the treatment of a disease associated with pathological angiogenesis in a mammal comprising the step of administering the antibody to the mammal.

The method of Item 17, wherein the disease is a cancer.

The method of Item 18, wherein the cancer is selected from the group consisting of a breast cancer, an ovarian cancer, an osteosarcoma, a liver cancer, a pancreatic cancer, a prostate cancer, a colorectal cancer, a non-small cell lung cancer, a renal cancer, a head and neck cancer, a melanoma, and a multiple myeloma.

The method of Item 19, wherein the treatment comprises the step of simultaneous or sequential administration of a second therapeutic agent with the antibody.

The method of Item 20, wherein the second therapeutic agent is selected from an anti-angiogenic agent, a chemotherapeutic agent, and a cytotoxic agent.

Use of the antibody according to any one of Items 1 to 10 for the manufacture of a medicament for the treatment of a disease associated with pathological angiogenesis in a mammal, preferably the disease is a cancer, and more preferably the cancer is selected from the group consisting of a breast cancer, an ovarian cancer, an osteosarcoma, a liver cancer, a pancreatic cancer, a prostate cancer, a colorectal cancer, a non-small cell lung cancer, a renal cancer, a head and neck cancer, a melanoma, and a multiple myeloma.

The invention further relates to use of the antibody according to any one of Items 1 to 10 for the detection of the AGR2 expression in a tissue or a cell sample of a patient.

The invention further relates to use of the antibody according to any one of Items 1 to 10 for the manufacture of a reagent, a kit or a formulation for the detection of the AGR2 expression in a tissue or a cell sample of a patient.

The invention relates to the hybridoma cell line 18A4. This hybridoma cell line was deposited in the China Center of Type Cell Collection (CCTCC) on Jan. 19, 2009 with a deposit number of CCTCC-C200902 at the address of the Wuhan University, Luojiashan, Wuchang, Wuhan, Hubei Province.

The binding of the antibody prepared by the aforesaid method according to the invention to AGR2 can be determined by employing a conventional technique in the art, for example, ELISA.

The preparation specifically comprises the following steps:

Step 1: Collection of the culture broth of the hybridoma cells.

Step 2: Purification of the monoclonal antibody.

The antibody obtained by the aforesaid method of preparation according to the invention can be used for blocking the promotion of tumor growth and metastasis by AGR2, specifically, for the inhibition of the growth rate of breast cancer cells (abnormal rate as compared to normal tissues) in vitro and the inhibition of the metastasis of tumor cells in vitro, and furthermore, for the inhibition of the growth, migration and invasive metastasis of the breast cancer cells T47D in vitro; and it can inhibit the cell cycle of the breast cancer cells T47D in vitro.

The abnormal growth rate refers to a growth rate exceeding that required for normal homeostasis in vivo and exceeding the growth rate of the normal tissues of the same origin.

The blocking or inhibition refers to the decrease or elimination of the active effect.

The inhibition of the growth rate of breast cancer cells in vitro refers to the increase or decrease of the number of the tumor cells in vitro. The in vitro regulation of the growth of the tumor cells can be determined by a known method in the art, for example, the MTT experiment as shown in the examples.

The inhibition of the metastasis of tumor cells in vitro refers to the alleviation of the migration and invasive metastasis of tumor cells in vitro. The in vitro regulation of tumor cell metastasis can be determined by a known method in the art, such as the transwell experiments as described in the examples.

BRIEF DESCRIPTION OF DRAWINGS

FIG. 1 shows the detection of AGR2 specificity by ELISA.

FIG. 2 shows the detection of AGR2 specificity by immunoblotting. A. 1. MCF7 cell lysate; 2. lysate of MB-231 transfected with AGR2-pcDNA3; 3. lysate of MB-231 transfected with pcDNA3; 4. lysate of 293T transfected with AGR2-pcDNA3; and 5. 293T transfected with pcDNA3. B. The monoclonal antibody can cross-react with murine AGR2.

FIG. 3 shows the detection of AGR2 specificity by immunoprecipitation.

FIG. 4 shows the detection of AGR2 specificity by immunofluorescence.

FIGS. 5A and 5B depicts the amino acid sequence alignment of the light chain variable region ($V_L$) (FIG. 5A) and the heavy chain heavy chain variable region ($V_H$) (FIG. 5B) (SEQ ID NO: 1 and 2, respectively) of the murine monoclonal antibody 18A4, the $V_L$ and $V_H$ domain of the humanized 18A4Hu1 version (SEQ ID NO: 3 and 4, respectively); and the consensus framework of the human $V_L$ and $V_H$ (hum κIII light chain κ subtype III; humI, heavy chain subtype I) (SEQ ID NO: 5 and 6, respectively). Asterisks identify the difference between the humanized 18A4Hu1 and the murine monoclonal antibody 18A4, or between the humanized 18A4Hu1 and the human consensus framework region. In order for comparison, the complementarity determining regions (CDR) are underlined.

FIGS. 6A and 6B depict the amino acid sequence alignment of the light chain variable region ($V_L$) (FIG. 2A) and heavy chain variable region ($V_H$) (FIG. 2B) of the murine monoclonal antibody 18A4 (SEQ ID NO: 1 and 2, respectively); the $V_L$ and $V_H$ domain of the humanized 18A4Hu1 version (SEQ ID NO: 3 and 4, respectively); and the consensus framework of human germline $V_L$ and $V_H$ (hum κIII light chain κ subtype III; humI, heavy chain subtype I) (SEQ ID NO: 5 and 6, respectively), as well as the consensus sequence of an approved drug generated using the germline VL and VH as templates. "-" indicates having the same amino acid as 18A4, and "*" indicates a position having a very different amino acid in the approved drug, suggesting that the change at that position has big influence on the affinity and specificity of the antibody.

FIG. 7 is a diagram for the construction of the plasmid for expressing the intact antibody. In the figure, Fragment 2 comprises IRES component, and Fragment 1 comprises the promoter, the terminator, the polyA tail, the resistant gene, etc., which are components that a conventional eukaryotic expression plasmid has.

FIG. 8 shows the SDS-PAGE electrophoresis of the purified antibody, with M representing a marker that indicates the size of the proteins. Lanes 1, 2, and 6 are samples of murine origin, and Lanes 3, 4, 7 and 8 are samples of human origin. The left panel is a non-denaturing gel, and the right panel is a denaturing gel. The gel stain is Coomassie Blue.

FIG. 9 shows the experimental results for the antibody affinity assayed by a competitive ELISA.

FIG. 10 shows the alignment of the mutated positions in the humanized antibody variant and the change of the number of the potential T cell epitopes. Red indicates an altered amino acid sequence.

FIG. 11 shows an antigen binding curve of the humanized antibody variant.

FIG. 12 shows the identification of the species specificity of the humanized antibody Agtuzumab by western blot. The left panel shows the result of SDS-PAGE staining, and the right panel shows the result of the western-blot using an HRP conjugated anti-human antibody as the secondary antibody. Lanes 1, 2 and 3 are murine 18A4 antibody, human IgG control antibody, and the humanized antibody Agtuzumab, respectively.

FIG. 13 shows the detection of the antigen binding specificity of the humanized antibody Agtuzumab by west blot. The left panel shows the result of SDS-PAGE staining, and the right panel uses the following primary antibodies, from left to right, a supernatant of a transfection with an empty plasmid, a supernatant of the Agtuzumab expression, a supernatant of an anti-GST negative control antibody, a supernatant of murine 18A4 antibody, a supernatant of an anti-MBP antibody, a supernatant of an anti-MBP antibody, a supernatant of a transfection with a control empty plasmid, a supernatant of Agtuzumab expression and a supernatant of an anti-GST negative control antibody, respectively.

FIG. 14 shows the detection of the binding specificity of the humanized antibody Agtuzumab to the antigens in the cell lysate by western blot. The left panel shows the result of SDS-PAGE staining, and the samples in Lanes 1, 2, 3 and 4 of the right panel are 293 T cells transfected with an AGR2 plasmid, 293 T cells not transfected with an AGR2 plasmid, MCF-7 (with natural AGR2 expression) cell lysate and purified AGR2-MBP, respectively, and the primary antibody is the humanized antibody Agtuzumab. The 26 KDa band is β-actin for presenting the relative amount of proteins in the lysate.

FIG. 15 shows the detection of the ability of the humanized antibody Agtuzumab to bind to the natural AGR in the MCF7 cells by immunoprecipitation (IP). Lanes 1, 2 and 3 are MCF7 cell lysate, proteins immunoprecipitated by protein G conjugated to human IgG, and proteins immunoprecipitated by protein G conjugated to the humanized antibody Agtuzumab. The primary antibody is an anti-AGR2 rabbit monoclonal antibody, and the secondary antibody is an HRP conjugated rabbit polyclonal antibody.

FIG. 16 shows AGR2-MBP mutants generated by mutations according to the analysis of potential epitopes of AGR2. Red GGG indicates that this position has been mutated to three glycines.

FIG. 17 shows the binding of the murine 18A4 and the humanized antibody Agtuzumab to the AGR2-MBP mutants. Lanes 1 to 12 are AGR2-MBP, AGR2-MBP mutants 1~10, and MBP, respectively.

FIG. 18 shows the detection of the ability of antibodies to inhibit the invasive metastasis of the liver cancer cell HepG2 in vitro by transwell experiments.

FIG. 19 shows the detection of the ability of antibodies to inhibit the growth and migration of the breast cancer cells T47D and MCF 7 in vitro by MTT.

FIG. 20 shows the detection of the ability of antibodies to inhibit the migration of the breast cancer cells T47D in vitro by wound healing assay.

FIG. 21 shows the detection of the ability of antibodies to inhibit the invasive metastasis of the liver cancer cell HepG2 in vitro by transwell experiments.

FIG. 22 shows the detection of the ability of antibodies to inhibit the cell cycle of the breast cancer cells MCF-7 and T47D in vitro by cytometry. FIG. 22A: after treating with the antibody of the invention for 48 h, inhibition of the cell cycle of the breast cancer cell T47D is detected. G1/G0 phase T47D cells increase by 8.56% compared to the control, while S phase and G2/M cells decrease by 8.56% accordingly. FIG. 22B: after treating with the antibody of the invention for 48 h, inhibition of the cell cycle of the breast cancer cell MCF-7 is detected. G1/G0 phase MCF-7 cells increase by 5.37% compared to the control, while S phase and G2/M cells decrease by 5.37% accordingly.

FIGS. 23, 24 and 25 show confirmation of the binding of the antibodies to the AGR2 active site domain by western blot.

FIG. 26A,B: Tumor growth of animal. C,D: Comparison of the tumor size between the treatment and control groups. E: Comparison of vessels.

DETAILED DESCRIPTION OF PREFERRED EMBODIMENTS

I. Definition

The terms "AGR2" and "human anterior gradient protein 2" can be used interchangeably herein, indicating the molecular family having the full length natural amino acid sequence of any AGR2 from human as mentioned above and the PDI superfamily to which AGR2 belongs, including potential forms and precursors, as well as the associated or unassociated complexes of the mature AGR2 ("potential AGR2"). Such AGR2s involved in the invention should be understood as any one of AGR2 types currently identified and to be identified in future, including a polypeptide derived from any AGR2 sequence and having at least about 75%, preferably at least about 80%, more preferably at least about 85%, still more preferably at least about 90%, and even more preferably at least about 95% homology thereto. The term "AGR2" refers to a gene encoding human AGR2. A preferably AGR is the natural sequence of human AGR2.

The term "antibody" herein is used with its most wide meaning, in particular, it encompasses intact monoclonal antibodies, polyclonal antibodies, multi-specific antibody formed from at least two intact antibodies (such as dual specific antibodies), and antibody fragments, as long as they show the desired biological activities.

An antibody "binding to" a target antigen, such as an AGR2 antigen refers to an antibody capable of binding to the antigen with sufficient affinity such that the antibody can be used as a therapeutic agent targeting cells expressing said antigen. If the antibody is an antibody binding to AGR2, then it usually preferentially binds to AGR2, rather than other members of the AGR2 family, and it is an antibody that does not significantly cross-reacts with other proteins in that family, e.g., BMP, activator protein, etc. An antibody having the "biological properties" of a given antibody, such as the monoclonal antibody designated as 18A4, refers to an antibody having one or more biological properties of said antibody, differing from other antibodies in that it binds to the same antigen (such as AGR2). For example, an antibody having the biological properties of 18A4 can block the activation of AGR2 and/or binds to the same AGR2 extracellular domain epitope as 18A4 does.

The term "monoclonal antibody" used herein refers to antibodies obtained from a substantially homogeneous antibody population, i.e., the various antibodies constituting the population are the same, except for possible naturally occurring mutants which usually exist in an extremely small amount. A monoclonal antibody is highly specific, i.e., against a single epitope on the antigen. Furthermore, different from a polyclonal antibody formulation comprising different antibodies against different determinant regions (epitopes), each monoclonal antibody is against a single determinant region on an antigen. In addition to their specificity, an advantage of the monoclonal antibodies is that they can now be synthesized free of contamination by other antibodies. The modifier "monoclonal" indicates the property of the antibody obtained from the substantially homogeneous antibody population, and should not be interpreted that any specific method is required to produce the antibody.

Unless otherwise specified, the "monoclonal antibody 18A4" refers to an antibody having the antigen binding residues of the murine 18A4 antibody in the following examples or an antibody derived from the murine 18A4 antibody in the following examples. For example, the monoclonal antibody 18A4 may be the murine monoclonal antibody 18A4 or a variant thereof, such as a humanized antibody 18A4 having the antigen binding amino acid residues of the murine monoclonal antibody 18A4. Examples of the humanized 18A4 antibody is provided in the following Example 2.

"Epitope 18A4" is the region in the AGR2 extracellular domain that the monoclonal antibody 18A4 binds to. In order to screen antibodies binding to the 18A4 epitope, a conventional cross block experiment can be conducted, as described in *Antibodies, A Laboratory Manual*, Cold Spring Harbor Laboratory, Ed Harlow and David Lane (1988).

The monoclonal antibody herein explicitly includes a "chimeric" antibody, in which a portion of the heavy chain and/or light chain is identical or homologous to the corresponding sequence derived from a specific species or belonging to a specific antibody type or subtype, and the remaining portion of the chain is identical or homologous to the corresponding sequence derived from another specific species or belonging to another specific antibody type or subtype, as well as fragments of such antibodies, as long as they display the desired biological activity.

An "intact" antibody is an antibody comprising the antigen binding variable region as well as the light chain constant region ($C_L$) and the heavy chain constant regions $C_H1$, $C_H2$ and $C_H3$. A constant region can be the constant region of a natural sequence (such as the constant region of a human natural sequence) or an amino acid sequence variant thereof. Preferably, an intact antibody has one or more effector function.

An "antibody fragment" comprises a portion of the intact antibody, preferably comprises its antigen binding or variable region. Examples of the antibody fragment include an Fab, an Fab', an F(ab')$_2$, an Fv fragment, a linear antibody, and a single chain antibody.

An "Fv" fragment is an antibody fragment comprising the intact antigen recognition and binding sites. This region consists of a heavy chain and a light chain variable region linked closely to each other, while the linkage can be covalent (such as in scFV). In such a conformation, the three CDRs in each variable region interact with each other to define the antigen binding site on the surface of the $V_H$-$V_L$ dimer.

An "Fab" fragment comprises the variable region and constant region of the light chain and the variable region and the first constant region (CH1) of the heavy chain. An F(ab')$_2$ antibody fragment comprises a pair of Fab fragments which are usually covalently linked at the vicinity of their carboxylic terminals via the hinge cysteines between them.

A "single chain Fv" or "scFv" antibody fragment comprises the VH and VL domains of an antibody that exist in a single polypeptide chain. Usually, the Fv polypeptide further comprises a polypeptide linker between the VH and VL domains which allows the scFv to form an ideal structure for binding to the antigen.

The term "linear antibody" comprises paired tandem Fd segments ($V_H$-$C_H1$-$V_H$-$C_H1$) which form paired antigen binding regions together with complementary light chain polypeptides. A linear antibody can be dual specific or single specific.

The term "antibody variable region" used herein refers to the light chain and heavy chain portions of the antibody molecule, which comprises the amino acid sequences of the complementarity determining region (CDRs, i.e., CDR1, CDR2 and CDR3) and framework regions (FRs). $V_H$ refers to the variable region of the heavy chain. $V_L$ refers to the variable region of the light chain. According to the method used in the invention, the designated amino acid position of CDRs and FRs can be defined by Kabat et al. (the numbering system described in Sequences of Proteins of Immunological Interest, $5^{th}$ Edition, Public Health Service, National Institutes of Health, Bethesda, Md. (1991)).

The term "complementarity determining region" (CDRs: i.e., CDR1, CDR2 and CDR3) used herein refers to amino acid residues in the variable regions of the antibody whose existence is necessary for antigen binding. Each variable region usually has three CDR regions identified as CDR1, CDR2 and CDR3. Each complementarity determining region can comprise the amino acid residues of the "complementarity determining region" defined by Kalat (i.e., roughly the residues (L1), 50-56 (L2) and 89-97 (L3) in the light chain variable region and 31-35 (H1), 50-65 (H2) and 95-102 (H3) in the heavy chain variable region.

A "framework region" (hereinafter FR) is those residues in the variable region other than the CDR residues. Each variable region usually has 4 FRs identified as FR1, FR2, FR3 and FR4. If the CDR is defined according to Kabat, the light chain FR residues roughly locate at the residues 1-23 (LCFR1), 35-49 (LCFR2), 57-88 (LCFR3), and 98-107 (LCFR4), and the heavy chain FR residues roughly locate at the residues 1-30 (HCFR1), 36-49 (HCFR2), 66-94 (HCFR3), and 103-113 (HCFR4) of the heavy chain residues. If the CDR comprises amino acid residues from a hypervariable loop, the light chain FR residues roughly locate at the residues 1-25 (LCFR1), 33-49 (LCFR2), 53-90 (LCFR3), and 97-107 (LCFR4) in the light chain, and the heavy chain FR residues roughly locate at the residues 1-25 (HCFR1), 33-52 (HCFR2), 56-95 (HCFR3), and 102-113 (HCFR4) of the heavy chain residues. In some cases where CDR comprises those amino acids of the CDR defined by Kabat the hypervariable loop, the FR residues are adjusted accordingly. For example, where CDRH1 comprises the amino acid H26-H35, the heavy chain FR1 residues locate at positions 1-25 and the FR2 residues locate at positions 36-49.

A "T cell epitope" used herein refers to a possible peptide stretch of a monoclonal antibody which can be bound and displayed by a MHC molecule and recognized by a T cell antigen receptor when the monoclonal antibody itself serves as a protein antigen. These peptide stretches contained in a monoclonal therapeutic antibody will increase the immune response of the patient to the therapeutic antibody. The larger the number of these peptide stretches, the higher is the probability that an immune response is caused.

A "humanized" form of a non-human (such as rodent) antibody refers to a chimeric antibody that at the minimum comprises a sequence derived from a non-human immunoglobin. To a large extent, the humanized antibody refers to an immunoglobin having the hypervariable region residues in a human immunoglobin (the recipient antibody) replaced with the hypervariable region residues of that of a non-human species, such as mouse, rat, rabbit or a non-human primate, having the desired specificity, affinity and ability (the donor antibody). In some cases, the framework region (FR) residues of a human immunoglobin are replaced with corresponding non-human residues. Moreover, the humanized antibody may comprise a residue not found in the recipient antibody or the donor antibody. These modifications are conducted to further improve the performance of the antibody. Usually, the humanized antibody will comprise substantially no less than at least one, usually two variable regions in which all or substantially all hypervariable loops correspond to the hypervariable loops of the non-human immunoglobin, and all or substantially all FRs are the FRs of the human immunoglobin sequence. Optionally, the humanized antibody will further comprise at least a portion of the constant region (Fc) of a immunoglobin, usually the constant region of the human immunoglobin.

An "anti-angiogenic agent" or an "angiogenic inhibitor" refers to a small molecule substance, a polynucleotide, a polypeptide, an isolated protein, a recombinant protein, an antibody, or a conjugate or fusion protein thereof that directly or indirectly inhibit angiogenesis, generation of vessels, or undesirable vessel permeability. It should be understood that anti-angiogenic agents includes those agents that bind to and block the angiogenic activity of an angiogenic factor or receptor thereof. Table 2 in *Oncogene*, 22:6549-6556 (2003) lists known anti-angiogenic factors. Table 1 in Sato *Int. J. Clin. Oncol.*, 8:200-206 (2003) lists the anti-angiogenic factors in clinical trials.

The term "abnormal angiogenesis" refers to an excessive, improper or runaway angiogenesis causing a disease state or deterioration thereof, wherein the disease state is, for example, a cancer, especially a solid tumor or metastatic tumor involving angiogenesis.

The term "cytotoxic agent" used herein refers to a substance that inhibits or blocks cell functions and/or causes cell disruption. This term is intended to include radioactive isotopes, chemotherapeutic agents and toxins.

A "chemotherapeutic agent" is a chemical compound used in the treatment of a cancer, also called an anti-neoplastic drug. An anti-nucleoplastic drug are usually classified, according to differences in the chemical structure and origin of the drug, into alkylating agents, anti-metabolic drugs, anti-neoplastic antibiotics, anthracycline antibiotics, anti-neoplastic herbal drugs, and hormones. Depending on the cycle or phase specificity, the chemotherapeutic drugs against tumor can be classified into (1) cell cycle non-specific agents (CCNSA), such as alkylating agent, anti-neoplastic antibiotics and platinum coordination complexes, etc., and (2) cell cycle specific agents (CCSA), such as anti-metabolic drugs, vinca alkaloids, etc.

II. Production of the Humanized Anti-AGR2 Antibody

A method for humanizing a non-human antibody has been described in the art. Preferably, a humanized antibody has one or more amino acid residues introduced from a non-human origin. These non-human amino acid residues are often called "input" residues which usually are taken from an "input" variable region. Humanization can essentially be conducted following the method of Winter and colleagues (Jones et al., *Nature*, 321: 522-525 (1986); Riechmann et al., *Nature*, 332: 323-327 (1988); and Verhoeyen et al., *Science*, 239: 1534-1536 (1988)), by replacing the hypervariable region sequence of a human antibody with corresponding sequences. Therefore, such a "humanized antibody" is a chimeric antibody (U.S. Pat. No. 4,816,567), in which a region essentially less than the complete human variable region is replaced with corresponding sequences from a non-human species. In practice, the humanized antibody is usually a human antibody in which some hypervariable residues and possibly some FR residues are replaced with the residues at the similar positions in a rodent antibody.

The choice of the human variable region for preparing the humanized antibody, including the light chain and the heavy chain, is very crucial for the reduction of antigenicity. Based on the so-called "best-fit" method, a whole library of known human variable region sequences is screened with the variable region sequences of a rodent antibody. Then, the human sequence closest to its rodent counterpart is selected as the human framework region (FR) of the humanized antibody (Sims et al., *J. Immunol.*, 151: 2296 (1993); Chothia et al., *J. Mol. Biol.*, 196: 901 (1987)). Another method makes use of a specific framework region derived from the consensus sequence of all human antibodies within a specific light chain or heavy chain subpopulation. The same framework can be used for several different humanized antibodies (Carter et al., *Proc. Natl. Acad. Sci. USA*, 89: 4285 (1992); Presta et al., *J. Immunol.*, 151: 2623 (1993)).

It is important for preparing the humanized antibody that the antibody is able to retain high affinity to the antigen and other advantageous biological properties after the humanization. The examples below describe the production of an exemplary humanized anti-AGR2 antibody that binds to AGR2.

The humanized antibody herein comprises non-human hypervariable region residues incorporated into the human heavy chain variable region, and comprises framework region (FR) substitution at positions selected from 57, 58, 60, 65, 67, 68 and/or 70, wherein the variable region numbers described in the numbering system described by Kabat et al. (Sequences of Proteins of Immunological Interest, 5$^{th}$ edition, Public Health Service, National Institutes of Health, Bethesda, Md. (1991) are used. In one embodiment, the humanized antibody comprises FR substitution at two or more positions selected from the positions 57, 58, 60, 65, 67, 68 and 70, while in a further embodiments, the humanized antibody comprises FR substitution at three or four positions selected from the positions 57, 58, 60, 65, 67, 68 and 70. In a preferred embodiment, the humanized antibody comprises FR substitutions at positions 65, 67, 68 and 70, or at positions 67, 68 and 70, or at positions 68 and 70. In a further preferred embodiment, the humanized antibody comprises FR substitutions at positions 57, 58 and 60, or at positions 57 and 60. It is preferred that the humanized antibody of the invention has less rather than more framework substitutions so as to minimize the antigenicity, but efficacy is also a very important factor to consider. The amino acids actually to be substituted are preferably those conservative amino acids so as not to change the immunogenicity or efficacy. Asparagine (N) at position 57 is preferably changed to serine (S), leucine (L) at position 58 is preferably changed to arginine (R), serine (S) at position 60 is preferably changed to threonine (T), lysine (K) at position 65 is preferably changed to glutamine (Q), lysine (K) at position 67 is preferably changed to arginine (R), alanine (A) at position 68 is preferably changed to valine (V), and leucine (L) at position 70 is preferably changed to methionine (M).

The exemplary humanized antibodies addressed in the invention comprises the complementarity determining residues DYNMD (SEQ ID NO: 8); DINPNYDTTS YNQKFKG or DINPNYDTTS YNQKFQG (SEQ ID NO: 9); and/or SMMGYGSPMD Y (SEQ ID NO: 10) of the heavy chain variable region, optionally comprises amino acid modifications of these CDR residues, for example, wherein these modifications substantially retain or improve the affinity of these antibodies. For example, the addressed antibody variants can have substitution of about 1 to 5 amino acids, about 1 to 4 amino acids, about 1 to 3 amino acids, and about 1 to 2 amino acids in the aforesaid heavy chain variable region CDR sequences. Such antibody variants can be prepared by, for example, affinity maturation. Preferably, the humanized antibody heavy chain variable region comprises two, most preferably all three of the CDR sequences of the complementarity determining residues DYNMD (SEQ ID NO: 8); DINPNYDTTS YNQKFKG or DINPNYDTTS YNQKFQG (SEQ ID NO: 9) and SMMGYGSPMD Y (SEQ ID NO: 10). The most preferable humanized antibody comprises the amino acid sequence of the heavy chain variable region of SEQ ID NO:4.

The humanized antibody of the invention can comprise the complementarity determining residues RASKSVSTSG YSYMH (SEQ ID NO: 11); LASNLES (SEQ ID NO: 12); and/or QHIRELPRT (SEQ ID NO: 13) of the light chain variable region. In a preferred embodiment, the light chain variable region complementarity determining residues described here are included in addition to the heavy chain variable region CDR residues in the aforesaid paragraphs. Such a humanized antibody optionally comprises amino acid modifications of the aforesaid light chain CDR residues, for example, wherein these modifications substantially retain or improve the affinity of these antibodies. For example, the addressed antibody variants can have substitution of about 1 to 5 amino acids, about 1 to 4 amino acids, about 1 to 3 amino acids, and about 1 to 2 amino acids in the aforesaid light chain variable region CDR sequences. Such antibody variants can be prepared by affinity maturation. Preferably, the humanized antibody light chain variable region comprises two, most preferably all three of the CDR sequences of the complementarity determining residues RASKSVSTSG YSYMH (SEQ ID NO: 11); LASNLES (SEQ ID NO: 12) and QHIRELPRT (SEQ ID NO: 13). The most preferable humanized antibody comprises the amino acid sequence of the light chain variable region as shown in SEQ ID NO: 3.

The application further addresses an affinity maturation antibody binding to AGR2. The parental antibody may be a human antibody or a humanized antibody, for example, an antibody comprising the light chain and/or heavy chain variable region sequences of SEQ ID NO: 3 and 4, respectively (i.e., version 5). The affinity maturation antibody preferably binds to AGR2 with an affinity superior to the murine anti-AGR2 monoclonal antibody 18A4 or variant 5 thereof (for example, its affinity is increased by, for example, about 2 times or about 4 times to about 100 times or about 1000 times as assessed by ELISA of the AGR2 extracellular domain (ECD)).

The invention encompasses many forms of the humanized antibody or the affinity maturation antibody thereof that bind to AGR2. For example, the humanized antibody or the affinity maturation antibody can be an antibody fragment, such as Fab, optionally conjugated to one or more cytotoxic agent so as to form an immunoconjugate. Alternatively, the humanized antibody or the affinity maturation antibody may be an intact antibody, such as an intact IgG antibody.

III. Vector, Host Cell and Recombination Method

The invention further provides an isolated nucleic acid encoding the humanized anti-AGR2 antibody, a vector and a host cell comprising the nucleic acid, as well as a recombinant technique for producing the antibody.

In order to recombinantly produce an antibody, a nucleic acid encoding the antibody is isolated and inserted in a reproducible vector for further cloning (DNA amplification) or expression. DNA encoding the monoclonal antibody can be conveniently isolated and sequenced using conventional procedures (such as using an oligonucleotide probe capable of specifically binding to genes encoding the heavy chain and the light chain). Many vectors can be obtained. The components of the vectors usually include but are not limited to one or more of the following: a signal sequence, a replication origin, one or more marker gene, an enhancer element, a promoter, and a transcription termination sequence.

(i) Signal Sequence Component

The anti-AGR2 antibody of the invention not only can be recombinantly produced directly but also can be produced as a fusion polypeptide with a heterologous polypeptide, which preferably has a signal sequence with a specific cleavage site at the N-terminal of the mature protein or polypeptide, or other polypeptide. A heterologous signal sequence recognized and processed (i.e., cleaved by a signal peptidase) by the host cell is preferred. For example, for yeast secretion, for example, yeast invertase leading sequence or α-factor leading sequence may be used. For expression in mammalian cells, mammalian signal sequence and viral secretory leading sequence such as Herpes simplex gD signal may be used.

Such precursor region DNA is linked to the open reading frame of the DNA encoding the anti-AGR2 antibody.

(ii) Replication Origin Component

Both the expression and cloning vectors comprise nucleic acid sequences enabling the vectors to replicate in one or more selected host cells. Generally, in the cloning vector, this sequence is a sequence enabling the vector to replicate independent to the host chromosomal DNA, including replication origin or self-replicating sequence. Such sequences for many bacteria, yeasts and viruses are well known.

(iii) Selective Gene Component

The expression and cloning antibody may comprise a selective gene, also called a selective marker. Typical selective genes encode the following proteins: (a) those imparting resistance to antibiotics or other toxins such as ampicillin, neomycin, methothrexate, or tetracyclin; (b) those rescuing auxotrophies; or (c) those providing key nutrients not obtainable from complex media, such as a gene encoding *Bacillus subtilis* D-alanine racemase.

(iv) Promoter Component

The expression and cloning vector usually comprise promoters recognized by the host organism and operably linked to the nucleic acid encoding the anti-AGR2 antibody.

(v) Enhancer Element Component

An enhancer sequence is often inserted into the vector to increase the transcription of the DNA encoding the anti-AGR2 antibody of the invention by a eukaryotic cell. Many enhancer sequences from mammalian genes are known. However, an enhancer from a eukaryotic cell virus is usually used.

(vi) Transcription Termination Component

The expression vector for a eukaryotic host cell will further comprise sequences necessary for the termination of transcription and stabilization of mRNA. Such sequences can usually be obtained from the 5' terminal and occasionally 3' terminal of the untranslated region of eukaryotic or viral DNA or cDNA. These regions comprise nucleotide segments that are transcribed into polyadenylated fragment in the untranslated portion of the mRNA encoding the anti-AGR2 antibody.

(vii) Selection and Transformation of Host Cells

Host cells suitable for cloning or expressing the DNA in the vector herein are the prokaryotes, yeasts, or high eukaryotic cells as described above. Prokaryotes suitable for this object include eubacteria, such as Gram negative or Gram positive organisms. In addition to prokaryotes, eukaryotic microorganisms such as filamentous fungi or yeasts are also suitable cloning or expressing hosts for the vector encoding the anti-AGR2 antibody.

The host cells suitable for the expression of glycosylated anti-AGR2 antibody are derived from multicellular organisms including plant. Examples of invertebrate cells include insect cells, for example, hosts such as *Spodoptera frugiperda*, etc.

However, vertebrate cells are of the most interest. Moreover, propagation of vertebrate cells in cultivation (tissue culture) has already become a conventional procedure. Examples of useful mammalian host cell lines are SV40 transformed monkey kidney CV1 line, human embryonic kidney line, baby hamster kidney cells, CHO cells, DG44 cells, DP12 cell line, etc.

In order to produce the anti-AGR2 antibody, the expression or cloning vectors described above are used to transform host cells and cultivated in a conventional nutrient media properly modified for inducing promoters, selecting transformants, or amplifying genes encoding desired sequences.

(viii) Culture of the Host Cells and Purification of the Anti-AGR2 Antibody

The host cells for producing the anti-AGR2 antibody of the invention can be cultivated in various commercial available media, such as RPMI-1640 (Sigma) and Dulbecco's modified Eagle's media (DMEM, Sigma). Further, necessary supplements known to a person skilled in the art, such as hormones and/or other growth factors, salts, buffer, antibiotics, trace elements, and glucose, can be added into these media as required. Cultivation conditions such as temperature, pH, etc. may be properly adjusted according to the selected host cell which is easy to a person of ordinary skill in the art.

When using a recombinant technique, the antibody can be generated in the cell or in the periplasmic space or directly secreted into the media. If the antibody is generated inside the cell, then first, the particulate debris of the host cells or lytic fragments are eliminated by, e.g., centrifugation or ultrafiltration. If the antibody is secreted into the media, the supernatant of such an expression system is usually first concentrated with a commercial protein concentrator. In any of the above steps, protease inhibitor may be included to inhibit proteolysis, and an antibiotic may be included to prevent the growth of foreign contaminants.

An antibody composition prepared from cells can be purified by using, e.g., hydroxyapatite chromatography, gel electrophoresis, dialysis, and affinity chromatography (the preferred purification technique is affinity chromatography). The suitability of protein A as the affinity ligand depends on the type and isotype of the immunoglobin Fc domain existing in the antibody. Depending on the antibody to be recovered, other protein purification techniques such as reverse phase HPLC, cation or anion exchange chromatography, SDS-PAGE and ammonium sulfate precipitation can also be used.

IV. Pharmaceutical Formulation

The therapeutic formulation of the antibody according to the invention is prepared by mixing the antibody having the desired purity with optionally a pharmaceutically acceptable carrier, expedient, or stabilizer and stored in a form of a lyophilized formulation or aqueous solution. The dosage and concentration used for the acceptable carrier, expedient, or stabilizer are non-toxic to the recipient, which is apparent to a person skilled in the art.

The formulation herein may further comprise more than one active compound required for treating the specific indications, preferably those compounds having complementary activity and no adverse effect against each other. The active compound, for example, can be a therapeutic agent, a cytotoxic agent, and/or anti-angiogenic agent, etc.

V. Formulation and Kit

In another embodiment of the invention, a formulation and a kit encompassing the antibody that can be used to treat the diseases as described in the invention or a pharmaceutical composition thereof are provided. This product comprises a vessel and a label or package insert attached to the vessel or placed separately in the package of the product. Suitable vessels include, for example, glasses, vials, injectors, etc. The vessel can be made using various materials such as glass or plastics. The vessel accommodates a pharmaceutical composition that is effective for the diseases described herein. The label or package insert indicates that the composition is used to treat the disease, such as a cancer, e.g., a breast cancer (e.g., a metastatic breast cancer), a prostate cancer, a lung cancer (for example, a non-small cell lung cancer), a colorectal cancer, etc.

Moreover, the product can include (a) a first vessel accommodating the composition comprising the monoclonal antibody of the invention, preferably a humanized monoclonal antibody; and (b) a second vessel accommodating the composition comprising a therapeutic agent other than the humanized antibody. The product of this embodiment of the invention may further comprise a package insert indicating that the first and second compositions can be combined for the treatment of, e.g., a cancer. Alternatively/additionally, the product may further comprise a second (or third) vessel accommodating a pharmaceutically acceptable buffer, such as bacteriostatic water for injection (BWFI) and phosphate-buffered saline. It may further comprise other substances that are necessary from a commercial or user perspective.

VI. Treatment Using the Anti-AGR2 Monoclonal Antibody

It is noted in the invention that the AGR2 antibody can be used for treating a tumor, such as a breast cancer, a pancreatic cancer, a prostate cancer, a colorectal cancer, a non-small cell lung cancer, a renal cancer, a liver cancer, a head and neck cancer, a melanoma, an ovarian cancer and a multiple myeloma, and the like.

Other regimens may be combined with the administration of the anti-AGR2 antibody. The combined administration includes simultaneous administration using separate formulation or as a single drug formulation and sequential administration according to either order, wherein preferably there exists a period of time when both two (or all) active agents exert their biological activity together.

In a preferred embodiment, two different anti-AGR2 antibodies are used to treat the patient. In another embodiment, the administration of one or more anti-AGR2 antibody is combined with the administration of an antibody against another tumor associated antigen. In another embodiment, the AGR antibody can be combined with an anti-angiogenic agent having inhibitory effect on angiogenesis.

In an embodiment, the treatment of the invention includes combined administration of the (one or more) anti-AGR2 antibody(s) and one or more mammalian immunomodulators, such as a cytokine, as well as a chemotherapeutic agent or growth inhibitor, including simultaneous administration of a mixture of different chemotherapeutic agents. Preferred chemotherapeutic agents include taxanes (such as taxol and docetaxel) and/or anthracycline antibiotics. The formulations and regimens of such chemotherapeutic agents can be used according to the instructions of the manufacturer or based on the experiences of a person skilled in the art.

The suitable dosage of any drugs administered in combination with the antibody of the invention may be the dosage used in a conventional therapy, but the dosage used may also be reduced because of the combined administration with the anti-AGR2 antibody of the invention.

The suitable dosage of the antibody of the invention can be properly adjusted between about 1 µg/kg and 15 mg/kg based on the type and severity of the disease. The administration may be in a form of single or multiple separate administration, but it may also be a continuous infusion. A typical daily dosage may be between about 1 µg/kg and 100 mg/kg, which depends on the object of the treatment, any prior therapy, the medical history and response to the antibody of the patient, as well as the discretion of the physician.

VII. Use of the Anti-AGR2 Monoclonal Antibody for Detection

The antibody of the invention (for example, the humanized anti-AGR2 antibody) also has non-therapeutic use. For example, the anti-AGR2 monoclonal antibody may also be used to detect the expression of the AGR2 protein in specific cells, tissues or sera.

For purpose of diagnosis, generally, a detection moiety, such as a radioactive isotope, a fluorescent label, or an enzyme-substrate label can be used to label the antibody. A person skilled in the art understands various techniques for accomplishing this object. For example, the antibody may be conjugated with biotin, alternatively, the antibody is conjugated with a small molecular hapten (such as digoxin).

The antibody of the invention can be used for any known assays, such as competitive binding assays, direct and indirect sandwich assays, and immunoprecipitation assays.

For convenience, the antibody of the invention can be provided in a kit, that is, a combination of a pre-quantified agent and an instruction for the diagnosis experiment. If an enzyme-labeled antibody is used, the kit will include the substrate and cofactor required for the enzyme (e.g., a substrate precursor providing a detectable chromophore or fluorophore). In addition, other additives such as stabilizers, buffer (for example, blocking buffer or lysis buffer) and the like may be included. The relative amount of various agents can be widely changed so as to provide concentrations of the agents in the solution that substantially optimize the sensitivity of the experiment. Specifically, these agents can be provided as dried powders, usually lyophilized, which comprises an expedient that provides an agent solution of a proper concentration upon dissolved.

EXAMPLES

Example 1

Production and Identification of the Monoclonal Antibody 18A4

A. Collection of the Hybridoma Cell Broth

Cells were continuously cultivated for three days using RPMI-1640 media (containing 10% bovine serum and 1% antibiotics) to keep the amount of the cells at 80% and ensure that the cells were in logarithmic phase, washed with PBS, exchanged into serum free RPMI-1640 media for 48 hours of cultivation before the supernatant was collected.

B. Purification of the Monoclonal Antibody

The antibody was purified using protein-G immunoaffinity chromatography according to the instructions of Pierce Protein G Agarose (20399). In brief, the protocol was as follows: the column material and all reagents were taken out of a 4° C. refrigerator and placed at room temperature such that they reached the room temperature; the column material is gently mixed and 2 ml 50% column material suspension was filled into the column, while caution was taken to avoid bubbles; 5 ml binding buffer was added to equilibrate the column; first, impurities were removed by filtration through 0.45 µm filter membrane, and then the sample was diluted with the binding buffer:sample at a ratio of 1:9 such that the salt concentration and pH value of the sample conformed to the requirements for binding; the diluted sample was loaded onto the column while the maximum binding was achieved with the total sample load was lower than 80% of the maximal binding capacity (5 mg mouse IgG/ml column material), otherwise the eluate will contain the antibody; the desired antibody was eluted using 5 ml elution buffer and collected at 1 ml/tube, with 100 µl 1M phosphate or Tris neutralization buffer added into the tubes before collection; and the protein concentration of each tube was determined using Coomassie Blue G-250. Samples with high protein concentration were mixed and the solution system was changed by dialysis using PBS (phosphate buffered saline). The column was regenerated using 12 ml elution buffer.

Example 2

Monoclonal Antibody Titer Assay

The procedure for assaying the antibody titer using ELISA was as follows: ELISA plates were coated at 100 µl/well (antigen concentration of 3 ug/ml, if the immunogen is a fusion protein, the label protein also needed for coating) and incubated overnight at 4° C. or 37° C. for 2 h. Solution was decanted and the plates were inverted and dumped dry. Blocking: 200 µl/well blocking solution was added for 4° C. overnight or 7° C. for 2 h, solution was decanted and the plates were inverted and dumped dry. The test samples were added at 100 µl/well (dilution factors: $0^2$, $10^3$, $10^4$, $10^5$, $10^6$, the positive and negative controls were diluted 1000 times at 100 µl/well) and incubated overnight at 4° C. or 37° C. for 2 h. Solution was decanted and the plates were inverted and dumped dry. The plates were washed with a washing buffer for 3×3 min and dumped dry. Addition of secondary antibody: the secondary antibody was diluted 1:10000 with the blocking buffer at 100 µl/well, after standing at 37° C. for 20 min, the plates were washed with a washing buffer for 3×3 min and dumped dry. Color development: the substrate was added at 100 µl/well to allow the color to develop to sufficient dark. Stopping: 100 µl stopping solution was added and the absorbance at 450 nm was read for the plate. The photo image of the plate was shown in FIG. 1, indicating that the titer of the antibody reached more than $10^6$.

Example 3

Specificity of the Monoclonal Antibody

A. Immunoblotting Detection:

Before lysis, cells were washed twice with 1×PBS, and scraped off by adding 10 ml PBS. After centrifugation at 1000 rpm for 5 min, the supernatant was discarded. 5 times volume of NP40 lysis buffer (with addition of protease inhibitors) was added and mixed thoroughly for a 20-min lysis. The tumor tissue was mixed thoroughly with 5 times volume of NP40 lysis buffer (with addition of protease inhibitors) for a 20-min lysis. After centrifugation at 15000 rpm at 4° C., the supernatant was recovered and the protein was quantified (the aforesaid lytic operations were all conducted on ice). Precipitates were suspended in 5×PAGE protein loading buffer (with addition of β-mercaptoethanol) and heated at 95° C. for 5 min. Proteins were separated using 15% SDS-PAGE agarose gel electrophoresis at a constant voltage of 80V for 2 h. The proteins were electrotransferred onto a nitrocellulose membrane at 400 mA for 45 min, and blocked at the room temperature using 5% bovine serum protein for 1 h. The proteins were hybridized with the primary antibody at the room temperature for 2 h, and washed with 1×PBST for 3×10 min. Primary antibodies and dilution factors: rabbit AGR2 antibody, 1:10000, β-actin 1:2000. The proteins were hybridized with the secondary antibody at the room temperature for 1 h and washed with 1×PBST for 3×10 min. The results were obtained by exposure, color development and scanning.

Results indicate that the monoclonal antibody detected the AGR2 expression in T47D and the 293T cells transfected with AGR2-pcDNA3, while no AGR2 expression was detected for the 293 T cells transfected with pcDNA3. See FIG. 2.

B. Immunoprecipitation

Sample preparation: 0.2 ml protein G (50% slurry Protein G Agarose from Pierce) was added into centrifugation tubes filled with 10 ml PBS and mixed thoroughly and allowed to stand at RT for 30 min. After centrifugation at 1500 rpm for 2 min, 10 ml supernatant was removed, to which 10 ml antibody (the antibody as shown in FIG. 3, with the isotype IgG used as the control antibody) containing medium was added and mixed thoroughly. After RT>2 hr or 4° C. overnight on a rocking platform, the supernatant was removed by centrifugation. The precipitates were washed twice with 10 ml PBS. Protein G beads with the antibody bound were transferred into 1.5 ml centrifugation tubes, to which PBS was added to 0.2 ml and kept at 4° C. Supernatants of T47D and MCF7 cells (24 hr) were collected and divided into two tubes of 10 ml each. One tube was subjected to immunoprecipitation using the protein G bound with the antibody of the invention to remove AGR2, while the other tube ad the protein G bound with the control antibody as control. After RT>2 hr or 4° C. overnight, centrifugation was conducted, and supernatant was collected to repeat the immunoprecipitation. The precipitates were washed for four times with 1 ml PBS, and suspended using 5×PAGE protein loading buffer (with addition of β-mercaptoethanol) and stood at 95° C. for 5 min. Results were detected by immunoblotting.

Results indicated that the monoclonal antibody detected the AGR2 in the supernatant of T47D and MCF7 through immunoprecipitation. See FIG. 3.

C. Immunofluorescence Detection

Circular coverslips were put into 24 well plates and rinsed with PBS once. They were further immersed with corresponding media before the media were sucked off. Trypsin digested T47D and MCF7 cells were transferred into the 24 well plates. After the cell adhered to the wall, the media were sucked off and washing was conducted with PBS once, followed by fixation with 4% formaldehyde at the room temperature for 10 to 20 minutes, washing with PBS once, 0.5% Triton X-100, and 0.3% sheep serum at the room temperature for 40 minutes. The primary antibody was added, followed by standing at 4° C. overnight and washing with PBS for 3×5 min. The fluorescent secondary antibody was added, followed by standing at the room temperature for 30 min and washing with PBS for 3×5 min. After DAPI staining for 2-5 min and PBS washing for 2×5 min, the observation was conducted with a fluorescent microscope on the sealed slides.

Results indicated that the monoclonal antibody detected the in situ AGR2 expression in the breast cancer cells T47D and MCF 7. See FIG. 4.

Example 4

Preparation of the Humanized 18A4 Antibody

First the variable region of the murine monoclonal antibody 18A4 was cloned into a vector capable of producing a mouse/human chimeric antibody. Total RNA was isolated from the hybridoma cells using the STRAGENE™ RNA extraction kit according to the protocols of the manufacturer. The variable region was amplified by RT-PCR, purified by gel electrophoresis, and inserted a derived plasmid containing the human κ constant region and human CH1 domain as described above. Plasmids were extracted and sequenced, resulting in the variable region sequence of the murine 18A4 monoclonal antibody heavy chain and light chain (SEQ ID NO: 1 and SEQ ID NO: 2).

The obtained 18A4 antibody sequences were subjected to alignment. Using the human antibody germline gene IGHV1-46*03 and IGKV3-20*02, which showed the highest homology, as templates, and based on the simulation of the 18A4 three dimensional structure and analysis on the approved antibody drug sequences, which used IGHV1-46*03 and IGKV3-20*02 as templates, to obtain the theoretic antibody sequence, the heavy chain amino acid sequence and light chain amino acid sequence of 18A4Hu1. The results of the alignment were shown in FIGS. 5 and 6. Based on the theoretic sequence, the antibody V region was synthesized using multiplex PCR, and the synthesized humanized antibody heavy chain variable region and humanized antibody light chain variable region were ligated into an expression plasmid, based on pGmax, for an antibody that contained the human IgG1 heavy chain constant region and the human light chain Kappa constant region by way of multiplex PCR. The construction of the expression plasmid for the intact antibody was shown in FIG. 7 (the sequence was SEQ ID NO: 7).

The successfully constructed 18A4 Hu1 antibody expression plasmid was used to transfect 293T cells for eukaryotic expression. Specifically, 2 mg/ml PEI and the expression plasmid were mixed at a ratio of 3:1 (w:w) as a transfection solution to transfect the 293T cells. After 6 hours, the cells were cultivated in a DMEM medium with 10% serum for 12 hours, and then switched to a serum free medium and cultivated for 4 days. The supernatant was recovered so as to obtain the antibody.

The obtained antibody supernatant was isolated and purified. Specifically, the supernatant was subjected to affinity chromatography using protein A. The isolated eluate, which contained the antibody, was subjected to dialysis so as to obtain a pure antibody 18A4Hu1. The concentration of the purified antibody was determined by A280 absorption or Coomassie Blue method. The purified antibody was subjected to SDS-PAGE electrophoresis analysis to further determine its purity (see FIG. 8).

The generated humanized antibody 18A4Hu1 was subjected to an affinity analysis and compared with the murine 18A4 antibody. Specifically, 3 ng/μl antigen AGR2 was used for coating the 96 well ELISA plates at 100 μl per well and blocked with blocking solution. Antibodies at 0.1 ng/μl were mixed 1:1 with antigens of different concentrations and incubated at 37 overnight, wherein the antigen concentration was serially diluted from 1000 nM. 100 μl incubated mixture was separately added into different ELISA plates and incubated at 37° C. for 1 hour. After washing the ELISA plates, the HRP-labeled secondary antibodies against human or mouse were added and incubated at 37° C. for 1 hour. Color development solutions A and B were added, each at 80 μl, and color was allowed to develop at 37° C. for 30 min. The reaction was stopped by adding 50 μl stopping solution and absorbance was determined at OD 450. Affinity plate was depicted and the affinities of the antibodies were calculated. The affinity plot for the murine antibody 18A4 and the humanized antibody 18A4Hu1 were shown in FIG. 9.

The humanized antibody 18A4Hu was subjected to T cell epitope analysis and individual amino acids were replaced for humanization to generate various humanized variants (information for variants was as shown in FIG. 10). Three heavy chain variants are shown in FIG. 10: YNQKFKG-KATLTV (SEQ ID NO. 16), YNQKFKGKVTMTV (SEQ ID NO. 17) and YNQKFKGRVTMTV (SEQ ID NO. 18), respectively. The antigen binding ability of the humanized variants was compared such that antibodies having less epitopes and higher affinity were selected, such as the antibody called Agtuzumab. See FIG. 11.

The generated humanized antibody Agtuzumab was characterized. The species specificity of Agtuzumab was analyzed using an anti-human secondary antibody to confirm that Agtuzumab was a humanized antibody (see FIG. 12). The antigen specificity of Agtuzumab was analyzed by western blot to confirm that it could specifically bind to expressed and purified AGR2-MBP protein (see FIG. 13), it could bind to AGR2 in the lysate of the AGR2 expressing MC7 cells (see FIG. 14), and it could bind to AGR2 in a natural state and detect the naturally secreted AGR2 in the supernatant of MCF7 by way of immunoprecipitation (IP) (see FIG. 15).

AGR2 was subjected to epitope analysis and multiple potential epitope amino acid positions were individually mutated (information of mutation was shown in FIG. 16). Epitope analysis was conducted by western blot using AGR2 mutants as the antigen and 18A4 and Agtuzumab as the primary antibody. FIG. 17 showed that 18A4 and the humanized antibody Agtuzumab shared consistent epitopes. The 11 sequences shown in FIG. 16 are designated as SEQ ID NOs. 19-29 from top of bottom of FIG. 16, respectively.

The affinity of Agtuzumab was determined and compared by competitive ELISA. FIG. 9 showed that Agtuzumab had similar affinity to murine 18A4, and slightly higher than 18A4Hu1. It had higher affinity and lower potential antigenicity.

The humanized antibody Agtuzumab was proved by tumor metastatic experiment to have the biological function of inhibiting the metastasis of HepG2, just as 18A4. See FIG. 18.

Example 5

Experiments of In Vitro Inhibition of Tumor Cell Growth

The MTT assay was as follows: MCF-7 and T47D cell lines were subcultured using corresponding cell culture medium to logarithmic phase (at least two passages, each grown to 80% confluent), digested with trypsin-EDTA solution, had the final cell concentration adjusted to between $5\times10^3$ and $5\times10^4$/ml, and seeded in 96 well plates at 200 μl per well. Each well was inspected to find out whether cells were evenly distributed. After the cell adhered, media without any antibody, with 20 μg/ml the antibody of the invention, or with 20 μg/ml control antibody IgG was added to each cell, respectively. After 48 h, to each well 20 μl 5 mg/ml MTT solution was added. After incubated for another 4 h, the original solution in each well of the 96 well plates was discarded and to each well 150 μl DMSO was then added to dissolve the formazan precipitates. After allowed to stand at the room temperature for 0.5 h, the plates were shaken on a rocking platform for 10 minutes. Absorbance of each well at 490 nm was determined using an ELISA reader.

Results indicated that the monoclonal antibody inhibited the growth of T47D cells and MCF-7 cells in vitro. See FIG. 19. The concentrations of the antibody of the invention and the control antibody IgG were both 20 μg/ml.

Example 6

Experiments of In Vitro Inhibition of Tumor Cell Migration

The procedure of the wound healing experiments was as follows: the breast cancer cell T47D, the ovarian cancer cell SKOV3, the osteosarcoma cell U2OS and the mouse fibroblast cell 3T3 were plated in 6-well plates (cells were 70% confluent). After confluence, the cells in the center were scraped off using a narrow cell scraper and washed with 1×PBS twice to wash off the scraped cells. The plates were photo imaged and marked. Media containing 20 μg/ml of the antibody of the invention or 20 μg/ml control antibody IgG were added. Timer was started, and photos were taken at 24 and 48 hours (be noted that the image should be taken at the same region as marked).

Results indicated that the monoclonal antibody inhibited the migration of the T47D, SKOV3, and 3T3 cells in vitro. See FIG. 20. The concentrations of the antibody of the invention and the control antibody IgG were both 20 μg/ml.

Example 7

Experiments of In Vitro Inhibition of Tumor Cell Metastasis

The transwell experiments were divided into 6 groups: 1: control, 2: MBP (25 ug/ml), 3: AGR2-MBP fusion protein (25 ug/ml), 4: AGR2-MBP (25 ug/ml)+IgG (25 ug/ml), 5: AGR2-MBP (25 ug/ml)+18A4 (25 ug/ml), 6: 18A4 (25 ug/ml).

The media in the transwell were all RPMI-1640 media+ 1% FBS.

In the experiment, first the outer well medium was added. The HepG2 and SKOV3 cells were digested with trypsin, counted and had the supernatant removed by centrifugation. Cell concentration was adjusted to $5\times10^5$/ml using RPMI-1640 medium containing 1% FBS. To each chamber 200 μl of said cells were added and cultivated in an cell incubator (5% $CO_2$, 37° C.). The timer was started and at 24 hours and 48 hours, the chamber was taken out and the cells in the inner chamber was scraped off. The chamber was placed in a methanol solution and fixed at the room temperature for 15 minutes. Staining was conducted with crystal violet for 15 minutes. Destaining was conducted with ethanol for 15 minutes. Then the chamber was put into PBS and had photos taken to count the number of cells that penetrated the membrane.

Results indicated that the antibody of the invention inhibited the metastasis of the liver cancer cells HepG2 and SKOV3 in vitro. See FIG. 21.

Example 8

Experiments of In Vitro Inhibition of Tumor Cell Cycle

The procedure for detecting the cell cycle using cytometry was as follows: T47D cell line was subcultured with corresponding cell culture medium to logarithmic phase (at least two passages, each grown to 80% confluent), digested with trypsin-EDTA solution and plated into 6 well plates. After cell adhered, the medium was changed to a medium containing 20 μg/ml of the antibody of the invention or 20 μg/ml of the control antibody IgG. The cells were digested using 1× trypsin at, 6, 12, 24, and 48 hours after the addition of the antibody. The cells were aspirated to single cells by adding 10 ml medium and collected into 15 ml centrifugation tube. The cells were collected by centrifugation at 200×g for 5 min. The supernatant was discarded and washed twice with 5 ml 1×PBS. After the supernatant was discarded, the cells were thoroughly suspended with 1 ml pre-cooled 1×PBS and added dropwise into pre-cooled 9 ml 70% ethanol, mixed thoroughly and incubated on ice for 1 h. Cells were collected by centrifugation at 200×g for 5 min, had supernatant discarded and washed for 3-4 h by adding 15 ml 1×PBS on ice. Cells were collected by centrifugation at 200×g for 5 min, had supernatant discarded, added with 500 μl PI staining buffer and transferred into 1.5 ml centrifugation tubes. Tubes were wrapped in aluminum foils, incubated at 37° C. for 30 min, and loaded onto the cytometer for detection of the cell cycle.

Results indicated that the monoclonal antibody inhibited the growth of the breast cancer cells T47D and MCF7 in vitro by increasing the G1/G0 phase and decreasing the S and G2/M phase in the cell cycle (FIG. 22).

Example 9

Determination of the Variable Region Sequence of the Monoclonal Antibody

The gene sequence of the antigen binding site of the blocking monoclonal antibody was determined as follows: RNA was extracted from the hybridoma cells. VL and VH were PCR amplified and had their gene sequence determined according to Marks et al. (Marks, J. D. et al., J. Mol. Biol., 222: 589-597, 1991). The primers used in the experiment were light chain 5'-GAGCGGATAACAATTTCACACA-GGA-3 ' (SEQ ID NO. 30), heavy chain 5'-CCACAATC-CCTGGGCACAA-3 ' (SEQ ID NO. 31), both for reverse sequencing.

Example 10

Determination of the Sequence of the Monoclonal Antibody Corresponding to the Epitopes The amino sequence of the monoclonal antibody corresponding to the epitopes of the antigen AGR2 was determined (see FIG. 23). The procedure was as followed: RNA was extracted from MCF cells. mRNA of AGR2 was obtained by PCR and reverse transcribed to obtain cDNA. The pcDNA3-AGR2-His eukaryotic expression plasmid was constructed and AGR2 was subjected to mutation by deletion. The upstream primer for the mutation was 5'-GT-TGCTTGTCTTGGATTTATATAGA-3', and the downstream primer was 5'-GCTGAAAATAAAGAAATCCA-GAAAT-3'. Such a mutation led to the deletion of the epitope PLMIIHHLDECPHSQALKKVFA. By western blot, it was found that the blocking monoclonal antibody no longer bound to the mutated AGR2 protein, thereby determining the amino acid sequence of the antibody that bound to the AGR2 epitope. Then AGR2 was subjected to point mutation. The upstream primer for the mutation was 5'-ATGAATAAT-CATCAAGGGTTTGTTGC-3', and the downstream primer was 5'-CACTTGGATGAGTGCCCACACA-3', wherein the "C" in the PDI active site "CXXS" was mutate to "S". The binding of the monoclonal antibody to this mutated protein was significantly weakened. It was determined that the monoclonal antibody specifically bound to the epitope "PLMIIHHLDECPHSQALKKVFA", and may inhibit the PDI activity. See FIGS. 24 and 25.

Example 11

In Vivo Animal Experiments for Antibody

SKOV3 cells at logarithmic phase were suspended in PBS and injected subcutaneously ($2\times10^6$ per animal) into 6 week old female BALB/c nude mice (180 to 220 g). The mice that had been injected with cells were randomized into two groups (8 mice per group): the PBS group and the 18A4 group. Four days after the injection of cells, intraperitoneal administration was started with 8 mg/kg 18A4 [1, 2] with the same volume of PBS as control. The administration was conducted twice per week and accompanied with the calculation of the size of tumors. The experiment was concluded after 14 weeks of drug treatment. The volume of the tumor was calculated with the following formula by reference to the publications of Herceptin and Avastin [3-5]: (L×W2)/2.

Results indicated that the monoclonal antibody inhibited tumor growth in vivo. See FIG. 26.

REFERENCES 1. van der Bij, G. J., et al., Experimentally induced liver metastases from colorectal cancer can be prevented by mononuclear phagocyte-mediated monoclonal antibody therapy. J Hepatol. 53(4): p. 677-85.

2. Bhuvaneswari, R., et al., Targeting EGFR with photodynamic therapy in combination with Erbitux enhances in vivo bladder tumor response. Mol Cancer, 2009. 8: p. 94.
3. Khalili, P., et al., Effect of Herceptin on the development and progression of skeletal metastases in a xenograft model of human breast cancer. Oncogene, 2005. 24(44): p. 6657-66.
4. Jerome, L., et al., Recombinant human insulin-like growth factor binding protein 3 inhibits growth of human epidermal growth factor receptor-2-overexpressing breast tumors and potentiates herceptin activity in vivo. Cancer Res, 2006. 66(14): p. 7245-52.
5. Guan, H., et al., Herceptin down-regulates HER-2/neu and vascular endothelial growth factor expression and enhances taxol-induced cytotoxicity of human Ewing's sarcoma cells in vitro and in vivo. Clin Cancer Res, 2005. 11(5): p. 2008-17.

The invention claimed is:

1. A humanized antibody or antigen binding fragment thereof capable of specifically binding human AGR2 protein, wherein said antibody binds a protein disulfide isomerase active domain of said human AGR2 protein, said humanized antibody comprising a light chain variable region and a heavy chain variable region, wherein the light chain variable region is identical to the sequence of SEQ ID No. 3 or has one, two or three amino acid substitutions at positions 57, 58, or 60 of SEQ ID NO: 3 (using the Kabat numbering), and wherein the heavy chain variable region is identical to the sequence of SEQ ID No. 4 or has one, two, three or four amino acid substitutions at positions 65, 67, 68 or 70 of SEQ ID NO: 4 (using the Kabat numbering), said substitutions at positions 57, 58, or 60 of SEQ ID NO: 3 being selected from the group consisting of N57S, L58R, S60T and combination thereof, said substitutions at positions 65, 67, 68 or 70 of SEQ ID NO: 4 being selected from the group consisting of K65Q, K67R, A68V, L70M and combination thereof.

2. A chimeric antibody or antigen binding fragment thereof capable of specifically binding to human AGR2 protein, wherein said antibody binds a protein disulfide isomerase active domain of said human AGR2 protein, said chimeric antibody comprising a light chain variable region and a heavy chain variable region, wherein the light chain variable region is identical to the sequence of SEQ ID No. 3 or has one, two or three amino acid substitutions at positions 57, 58, or 60 of SEQ ID NO: 3 (using the Kabat numbering), and wherein the heavy chain variable region is identical to the sequence of SEQ ID NO. 4 or has one, two, three or four amino acid substitutions at positions 65, 67, 68 or 70 of SEQ ID NO: 4 (using the Kabat numbering), said substitutions at positions 57, 58, or 60 of SEQ ID NO: 3 being selected from the group consisting of N57S, L58R, S60T and combination thereof, said substitutions at positions 65, 67, 68 or 70 of SEQ ID NO: 4 being selected from the group consisting of K65Q, K67R, A68V, L70M and combination thereof.

3. The antibody or antigen binding fragment of claim 1, wherein said humanized antibody binds an AGR2 epitope that is the same as the AGR2 epitope bound by monoclonal antibody 18A4.

4. The antibody or antigen binding fragment of claim 1, wherein said AGR2 active domain comprises the sequence of SEQ ID No. 14.

5. The antibody or antigen binding fragment of claim 1, wherein said antibody is a humanized intact IgG1 antibody.

6. The antibody or antigen binding fragment of claim 1, wherein antigen binding fragment is selected from the group consisting of a Fab, a Fab', a F(ab')2, a Fv, a linear antibody, and a single chain antibody.

7. A pharmaceutical composition comprising the antibody or antigen binding fragment of claim 1 and a pharmaceutically acceptable carrier.

8. An isolated nucleic acid encoding the antibody or antigen binding fragment of claim 1.

9. A vector comprising the isolated nucleic acid of claim 8.

10. An isolated host cell comprising the vector of claim 9.

11. A method for producing an antibody comprising cultivating the host cell of claim 10 in a culture under conditions sufficient to produce an antibody capable of specifically binding to human AGR2 protein.

12. The method of claim 11, further comprising recovering the antibody from the culture of the host cell.

13. A method to treat a cancer associated with pathological angiogenesis in a mammal, comprising the step of administering the antibody of claim 1 to the mammal with said cancer.

14. The method of claim 13, wherein the cancer is selected from the group consisting of breast cancer, ovarian cancer, osteosarcoma, liver cancer, pancreatic cancer, prostate cancer, colorectal cancer, non-small cell lung cancer, renal cancer, head and neck cancer, melanoma, and multiple myeloma.

15. The method of claim 13, wherein the treatment comprises the step of simultaneous or sequential administration of a second therapeutic agent.

16. The method of claim 15 wherein the second therapeutic agent is selected from the group consisting of an anti-angiogenic agent, a chemotherapeutic agent, and a cytotoxic agent.

17. The antibody or antigen binding fragment of claim 1, wherein the light chain variable region is identical to the sequence of SEQ ID No. 3, and wherein the heavy chain variable region comprises the K65Q, K67R, A68V and L70M substitutions.

* * * * *

SEQUENCE LISTING

```
<160> NUMBER OF SEQ ID NOS: 29

<210> SEQ ID NO 1
<211> LENGTH: 111
<212> TYPE: PRT
<213> ORGANISM: Artificial
<220> FEATURE:
<223> OTHER INFORMATION: Light chain variable region (VL) sequence of
      18A4

<400> SEQUENCE: 1

Asp Ile Val Leu Thr Gln Ser Pro Ala Ser Leu Thr Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Arg Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Gly Glu Asp Ala Ala Thr Tyr Tyr Cys Gln His Ile Arg
                85                  90                  95

Glu Leu Pro Arg Thr Phe Gly Gly Gly Thr Lys Leu Glu Ile Lys
            100                 105                 110

<210> SEQ ID NO 2
<211> LENGTH: 120
<212> TYPE: PRT
<213> ORGANISM: Artificial
<220> FEATURE:
<223> OTHER INFORMATION: Heavy chain variable region (VH) sequence of
      18A4

<400> SEQUENCE: 2

Glu Val Gln Leu Gln Gln Phe Gly Ala Glu Leu Val Lys Pro Gly Ala
1               5                   10                  15

Ser Val Lys Ile Ser Cys Lys Ala Ser Ala Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Tyr Asp Thr Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Ser Met Met Gly Tyr Gly Ser Pro Met Asp Tyr Trp Gly Gln
            100                 105                 110

Gly Thr Ser Val Thr Val Ser Ser
```

<210> SEQ ID NO 3
<211> LENGTH: 111
<212> TYPE: PRT
<213> ORGANISM: Artificial
<220> FEATURE:
<223> OTHER INFORMATION: VL sequence of humanized 18A4HU1 version

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Arg Leu Glu Pro Glu Asp Phe Ala Val Tyr Tyr Cys Gln His Ile Arg
                85                  90                  95

Glu Leu Pro Arg Thr Phe Gly Gly Gly Thr Lys Leu Glu Ile Lys
            100                 105                 110

<210> SEQ ID NO 4
<211> LENGTH: 120
<212> TYPE: PRT
<213> ORGANISM: Artificial
<220> FEATURE:
<223> OTHER INFORMATION: VH sequence of humanized 18A4HU1 version

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Ile
        35                  40                  45

Gly Asp Ile Asn Pro Asn Tyr Asp Thr Thr Ser Tyr Asn Gln Lys Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Met Met Gly Tyr Gly Ser Pro Met Asp Tyr Trp Gly Gln
            100                 105                 110

Gly Thr Leu Val Thr Val Ser Ser
        115                 120

<210> SEQ ID NO 5
<211> LENGTH: 102
<212> TYPE: PRT
<213> ORGANISM: Artificial
<220> FEATURE:
<223> OTHER INFORMATION: Amino acid sequence of VL consensus framework
      (hum kappaIII, light chain kappa subtype III)

<400> SEQUENCE: 5

Glu Ile Val Leu Thr Gln Ser Pro Ala Thr Leu Ser Leu Ser Pro Gly

```
           1               5                  10                 15
         Glu Arg Ala Thr Leu Ser Cys Arg Ala Ser Gln Ser Val Ser Ser
                        20                 25                 30

Tyr Leu Ala Trp Tyr Gln Gln Lys Pro Gly Gln Ala Pro Arg Leu Leu
                     35                 40                 45

Ile Tyr Gly Ala Ser Ser Arg Ala Thr Gly Ile Pro Ala Arg Phe Ser
                 50                 55                 60

Gly Ser Gly Ser Gly Thr Asp Phe Thr Leu Thr Ile Ser Arg Leu Glu
         65                 70                 75                 80

Pro Glu Asp Phe Ala Val Tyr Tyr Cys Gln Trp Thr Phe Gly Gly Gly
                         85                 90                 95

Thr Lys Leu Glu Ile Lys
                     100
```

<210> SEQ ID NO 6
<211> LENGTH: 113
<212> TYPE: PRT
<213> ORGANISM: Artificial
<220> FEATURE:
<223> OTHER INFORMATION: Amino acid sequence of VH consensus framework
      (humI, heavy chain subtype I)

<400> SEQUENCE: 6

```
         Gln Val Gln Leu Val Gln Ser Gly Ala Glu Val Lys Lys Pro Gly Ala
         1               5                  10                 15

Ser Val Lys Val Ser Cys Lys Ala Ser Gly Tyr Thr Phe Thr Ser Tyr
                         20                 25                 30

Tyr Met His Trp Val Arg Gln Ala Pro Gly Gln Gly Leu Glu Trp Met
                     35                 40                 45

Gly Ile Ile Asn Pro Ser Gly Gly Ser Thr Ser Tyr Ala Gln Lys Phe
                 50                 55                 60

Gln Gly Arg Val Thr Met Thr Arg Asp Thr Ser Thr Ser Thr Val Tyr
         65                 70                 75                 80

Met Glu Leu Ser Ser Leu Arg Ser Glu Asp Thr Ala Val Tyr Tyr Cys
                         85                 90                 95

Ala Arg Tyr Phe Asp Tyr Trp Gly Gln Gly Thr Leu Val Thr Val Ser
                     100                105                110

Ser
```

<210> SEQ ID NO 7
<211> LENGTH: 8775
<212> TYPE: DNA
<213> ORGANISM: Artificial
<220> FEATURE:
<223> OTHER INFORMATION: Sequence of plasmid construct for
      expressing 18A4Hu1 intact antibody

<400> SEQUENCE: 7

```
catatgagcg cccaatacgc aaaccgcctc tccccgcgcg ttggccgatt cattaatgca     60
gctggcacga caggtttccc gactggaaag cgggcagtga gcgcaacgca attaatgtga    120
gttagctcac tcattaggca ccccaggctt tacactttat gcttccggct cgtatgttgt    180
gtggaattgt gagcggataa caatttcaca caggaaacag ctatgaccat gattacgcca    240
agcttccagg ctccccagca ggcagaagta tgcaaagcat gcatctcaat tagtcagcaa    300
ccatagtccc gcccctaact ccgcccatcc cgcccctaac tccgcccagt tccgcccatt    360
ctccgcccca tggctgacta attttttttta tttatgcaga ggccgaggcc gcctcggcct    420
```

```
ctgagctatt ccagaagtag tgaggaggct tttttggagg cctaggcttt tgcaaaaagc      480
tttgcaaaga tggataaagt tttaaacaga gaggaatctt tgcagctaat ggaccttcta      540
ggtcttgaaa ggagtgggaa ttggctccgg tgcccgtcag tgggcagagc gcacatcgcc      600
cacagtcccc gagaagttgg ggggaggggt cggcaattga accggtgcct agagaaggtg      660
gcgcggggta aactgggaaa gtgatgtcgt gtactggctc cgccttttc ccgagggtgg       720 gggagaaccg tatataagtg cagtagtcgc cgtgaacgtt cttttcgca acgggtttgc       780 cgccagaaca caggtaagtg ccgtgtgtgg ttcccgcggg cctggcctct ttacgggtta      840
tggcccttgc gtgccttgaa ttacttccac gcccctggct gcagtacgtg attcttgatc      900
ccgagcttcg ggttggaagt gggtgggaga gttcgaggcc ttgcgcttaa ggagccccctt    960 cgcctcgtgc ttgagttgag gcctggcctg ggcgctgggg ccgccgcgtg cgaatctggt     1020
ggcaccttcg cgcctgtctc gctgcttcg ataagtctct agccatttaa aattttgat      1080 gacctgctgc gacgctttt ttctggcaag atagtcttgt aaatgcgggc caagatctgc      1140
acactggtat ttcggttttt ggggccgcgg gcggcgacgg ggcccgtgcg tcccagcgca     1200
catgttcggc gaggcgggc ctgcgagcgc ggccaccgag aatcggacgg gggtagtctc      1260
aagctggccg gcctgctctg gtgcctggcc tcgcgccgcc gtgtatcgcc ccgccctggg     1320
cggcaaggct ggcccggtcg gcaccagttg cgtgagcgga aagatggccg cttcccggcc     1380
ctgctgcagg gagctcaaaa tggaggacgc ggcgctcggg agagcgggcg ggtgagtcac     1440
ccacacaaag gaaaagggcc tttccgtcct cagccgtcgc ttcatgtgac tccacggagt     1500
accgggcgcc gtccaggcac ctcgattagt tctcgagctt ttggagtacg tcgtctttag     1560 gttggggga ggggttttat gcgatggagt ttccccacac tgagtgggtg gagactgaag      1620
ttaggccagc ttggcacttg atgtaattct ccttggaatt tgcccttttt gagtttggat     1680
cttggttcat tctcaagcct cagacagtgg ttcaaagttt ttttcttcca tttcaggtgt     1740
cgtgaggaat tctctagaga tccctcccga tatcgtttaa acatggacat gagggttcct    1800
gctcagctcc tgggactcct gctgctctgg ctcccaggtg ccagatgtga gattgtgctg    1860
acacagtctc ctgccacctt atctctctct ccaggggaga gggccaccct gagctgcagg    1920
gccagcaaga gtgtcagtac atctggctat agttatatgc actggtacca acagaaacca    1980
ggccaggccc ccagactcct catctatctt gcatctaacc tagaatctgg gatccctgct    2040
agattcagtg gcagtgggtc tgggacagac ttcacactca ccatcagcag gctggaacct    2100
gaggacttcg ctgtgtatta ctgtcagcac attagagagc ttcctcggac gttcggtgga    2160
ggcaccaagc tggaaatcaa acgaactgtg gctgcaccat ctgtcttcat cttcccgcca    2220
tctgatgagc agttgaaatc tggaactgcc tctgttgtgt gcctgctgaa taacttctat    2280
cccagagagg ccaaagtaca gtggaaggtg gataacgccc tccaatcggg taactcccag    2340
gagagtgtca cagagcagga cagcaaggac agcacctaca gcctcagcag caccctgacg    2400
ctgagcaaag cagactacga gaaacacaaa gtctacgcct gcgaagtcac ccatcagggc    2460
ctgagctcgc ccgtcacaaa gagcttcaac aggggagagt gttagggatc cgcccctctc    2520
cctccccccc ccctaacgtt actggccgaa gccgcttgga ataaggccgg tgtgcgtttg    2580
tctatatgtt attttccacc atattgccgt cttttggcaa tgtgagggcc cggaaacctg    2640
gccctgtctt cttgacgagc attcctaggg gtctttcccc tctcgccaaa ggaatgcaag    2700
gtctgttgaa tgtcgtgaag gaagcagttc ctctggaagc ttcttgaaga caaacaacgt    2760
ctgtagcgac ccttttgcagg cagcggaacc ccccacctgg cgacaggtgc ctctgcggcc    2820
```

```
aaaagccacg tgtataagat acacctgcaa aggcggcaca accccagtgc cacgttgtga    2880
gttggatagt tgtggaaaga gtcaaatggc tctcctcaag cgtattcaac aaggggctga    2940
aggatgccca gaaggtaccc cattgtatgg gatctgatct ggggcctcgg tacacatgct    3000
ttacatgtgt ttagtcgagg ttaaaaaaac gtctaggccc cccgaaccac ggggacgtgg    3060
tttttccttt g aaaaacacga tgataatatg ccacaacca tggactggac ctggagcatc    3120
cttttcttgg tggcagcagc aacaggtgcc cactcccagg tccagctggt gcagtctgga    3180
gctgaggtga agaagcctgg agcttcagtg aaggtttcct gcaaggcttc tggatacaca    3240
ttcactgact acaacatgga ctgggttcga caggcccctg gacagggcct tgagtggatt    3300
ggagatatta atcctaacta tgacactact agctacaacc agaagttcca gggcagagtg    3360
acaatgactg tggacaagtc cacgagcaca gcctacatgg agctcagcag cctgagatct    3420
gaggacactg cagtctatta ctgtgcaaga tcgatgatgg gatatggttc ccctatggac    3480
tactggggtc aaggcacact ggtcaccgtc tcctcagcct ccaccaaggg cccatcggtc    3540
ttccccctgg caccctcctc caagagcacc tctgggggca gcagccct gggctgcctg    3600 gtcaaggact acttccccga accggtgacg gtgtcgtgga actcaggcgc cctgaccagc    3660
ggcgtgcaca ccttcccggc tgtcctacag tcctcaggac tctactccct cagcagcgtg    3720
gtgaccgtgc cctccagcag cttggacacc cagacctaca tctgcaacgt gaatcacaag    3780
cccagcaaca ccaaggtgga caagaaagtt gagcccaaat cttgtgacaa aactcacaca    3840
tgcccaccgt gcccagcacc tgaactcctg ggggaccgt cagtcttcct cttccccca    3900 aaacccaagg acaccctcat gatctcccgg acccctgagg tcacatgcgt ggtggtggac    3960
gtgagccacg aagaccctga ggtcaagttc aactggtacg tggacggcgt ggaggtgcat    4020
aatgccaaga caaagccgcg ggaggagcag tacaacagca cgtaccgtgt ggtcagcgtc    4080
ctcaccgtcc tgcaccagga ctggctgaat ggcaaggagt acaagtgcaa ggtctccaac    4140
aaagccctcc cagcccccat cgagaaaacc atctccaaag ccaaagggca gccccgagaa    4200
ccacaggtgt acaccctgcc cccatcccgg gatgagctga ccaagaacca ggtcagcctg    4260
acctgcctgg tcaaaggctt ctatcccagc gacatcgccg tggagtggga gagcaatggg    4320
cagccggaga caactacaa gaccacgcct cccgtgctgg actccgacgg ctccttcttc    4380
ctctacagca agctcaccgt ggacaagagc aggtggcagc aggggaacgt cttctcatgc    4440
tccgtgatgc atgaggctct gcacaaccac tacacacaga gagcctctcc cctgtctccg    4500
ggtaaatagg tgagcaaggg cgaggagctg ttcaccgggg tggtgcccat cctggtcgag    4560
ctggacggcg acgtaaacgg ccacaagttc agcgtgtccg gcgagggcga gggcgatgcc    4620
acctacggca agctgaccct gaagttcatc tgcaccaccg gcaagctgcc cgtgccctgg    4680
cccaccctcg tgaccaccct gacctacggc gtgcagtgct tcagccgcta ccccgaccac    4740
atgaagcagc acgacttctt caagtccgcc atgcccgaag gctacgtcca ggagcgcacc    4800
atcttcttca aggacgacgg caactacaag acccgcgccg aggtgaagtt cgagggcgac    4860
accctggtga accgcatcga gctgaagggc attgacttca aggaggacgg caacatcctg    4920
gggcacaagc tggagtacaa ctacaacagc cacaacgtat atatcatggc cgacaagcag    4980
aagaacggca tcaaggtgaa cttcaagatc cgccacaaca tcgaggacgg cagcgtgcag    5040
ctcgccgacc actaccagca gaacacccc atcggcgacg gccccgtgct gctgcccgac    5100
aaccactacc tgagcatcca gtccgccctg agcaaagacc ccaacgagaa gcgcgatcac    5160
```

-continued

```
atggtcctgc tggagttcgt gaccgccgcc gggatcactc tcggcatgga cgagctgtac      5220
aagtaaagcg gccgcgactc tagagtgagg gtccccacct gggacccttg agagtatcag      5280
gtctcccacg tgggagacaa gaaatccctg tttaatattt aaacagcagt gttccccatc      5340
tgggtccttg caccccctcac tctggcctca gccgactgca cagcggcccc tgcatcccct     5400
tggctgtgag gcccctggac aagcagaggt ggccagagct gggaggcatg gccctggggt      5460
cccacgaatt tgctggggaa tctcgttttt cttcttaaga cttttgggac atggtttgac      5520
tcccgaacat caccgacgcg tctcctgttt ttctgggtgg cctcgggaca cctgccctgc      5580
ccccacgagg gtcaggactg tgactctttt tagggccagg caggtgcctg gacatttgcc      5640
ttgctggacg gggactgggg atgtgggagg gagcagacag gaggaatcat gtcaggcctg      5700
tgtgtgaaag gaagctccac tgtcaccctc cacctcttca cccccactc accagtgtcc       5760
cctccactgt cacattgtaa ctgaacttca ggataataaa gtgtttgcct ccaaaaaaaa      5820
aaaaaaaaaa aaaaaaaaaa aaaaaaaaaa aaaaaaaaaa aaaaaaaaaa aaaaaaaaaa      5880
aaaaaaaaaa aaaaaaaaaa aagaattcac tggccgtcgt tttacaacgt cgtgactggg      5940
aaaaccctgg cgttacccaa cttaatcgcc ttgcagcaca tccccctttc gccagctggc      6000
gtaatagcga agaggcccgc accgatcgcc cttcccaaca gttgcgcagc ctgaatggcg      6060
aatggcgcct gatgcggtat tttctcctta cgcatctgtg cggtatttca caccgcatac      6120
gtcaaagcaa ccatagtacg cgccctgtag cggcgcatta gcgcggcgg gtgtggtggt       6180
tacgcgcagc gtgaccgcta cacttgccag cgccctagcg cccgctcctt tcgctttctt      6240
cccttccttt ctcgccacgt tcgccggctt tccccgtcaa gctctaaatc gggggctccc      6300
tttagggttc cgatttagtg ctttacggca cctcgacccc aaaaaacttg atttgggtga      6360
tggttcacgt agtgggccat cgccctgata acggtttttt cgcccttga cgttggagtc       6420
cacgttcttt aatagtggac tcttgttcca aactggaaca cactcaacc ctatctcggg       6480
ctattctttt gatttataag ggattttgcc gatttcggcc tattggttaa aaaatgagct      6540
gatttaacaa aaatttaacg cgaattttaa caaaatatta cgtttacaa ttttatggtg       6600
cactctcagt acaatctgct ctgatgccgc atagttaagc cagccccgac acccgccaac      6660
acccgctgac gcgccctgac gggcttgtct gctcccggca tccgcttaca gacaagctgt      6720
gaccgtctcc gggagctgca tgtgtcagag gttttcaccg tcatcaccga aacgcgcgag      6780
acgaaagggc ctcgtgatac gcctattttt ataggttaat gtcatgataa taatggtttc      6840
ttagacgtca ggtggcactt ttcggggaaa tgtgcgcgga accctatttt gtttattttt      6900
ctaaatacat tcaaatatgt atccgctcat gagacaataa ccctgataaa tgcttcaata     6960
atattgaaaa aggaagagta tgagtattca acatttccgt gtcgccctta ttcccttttt     7020
tgcggcattt tgccttcctg ttttgctca cccagaaacg ctggtgaaag taaaagatgc      7080
tgaagatcag ttgggtgcac gagtgggtta catcgaactg gatctcaaca gcggtaagat     7140
ccttgagagt tttcgccccg aagaacgttt tccaatgatg agcacttta aagttctgct      7200
atgtggcgcg gtattatccc gtattgacgc cgggcaagag caactcggtc gccgcataca    7260
ctattctcag aatgacttgg ttgagtactc accagtcaca gaaaagcatc ttacggatgg     7320
catgacagta agagaattat gcagtgctgc cataaccatg agtgataaca ctgcggccaa     7380
cttacttctg acaacgatcg gaggaccgaa ggagctaacc gcttttttgc acaacatggg     7440
ggatcatgta actcgccttg atcgttggga accggagctg aatgaagcca taccaaacga     7500
cgagcgtgac accacgatgc ctgtagcaat ggcaacaacg ttgcgcaaac tattaactgg     7560
```

```
cgaactactt actctagctt cccggcaaca attaatagac tggatggagg cggataaagt   7620
tgcaggacca cttctgcgct cggcccttcc ggctggctgg tttattgctg ataaatctgg   7680
agccggtgag cgtgggtctc gcggtatcat tgcagcactg gggccagatg gtaagccctc   7740
ccgtatcgta gttatctaca cgacggggag tcaggcaact atggatgaac gaaatagaca   7800
gatcgctgag ataggtgcct cactgattaa gcattggtaa ctgtcagacc aagtttactc   7860
atatatactt tagattgatt taaaacttca ttttttaattt aaaaggatct aggtgaagat   7920 ccttttttgat aatctcatga ccaaaatccc ttaacgtgag ttttcgttcc actgagcgtc   7980
agaccccgta gaaagatca aaggatcttc ttgagatcct ttttttctgc gcgtaatctg   8040
ctgcttgcaa acaaaaaaac caccgctacc agcggtggtt tgtttgccgg atcaagagct   8100
accaactctt tttccgaagg taactggctt cagcagagcg cagataccaa atactgtcct   8160
tctagtgtag ccgtagttag gccaccactt caagaactct gtagcaccgc ctacatacct   8220
cgctctgcta atcctgttac cagtggctgc tgccagtggc gataagtcgt gtcttaccgg   8280
gttggactca agacgatagt taccggataa ggcgcagcgg tcgggctgaa cggggggttc   8340
gtgcacacag cccagcttgg agcgaacgac ctacaccgaa ctgagatacc tacagcgtga   8400
gctatgagaa agcgccacgc ttcccgaagg agaaaggcg gacaggtatc cggtaagcgg   8460
cagggtcgga acaggagagc gcacgaggga gcttccaggg ggaaacgcct ggtatctta   8520 tagtcctgtc gggtttcgcc acctctgact tgagcgtcga ttttttgtgat gctcgtcagg   8580 ggggcggagc ctatggaaaa acgccagcaa cgcggccttt ttacggttcc tggccttttg   8640
ctggcctttt gctcacatgt tctttcctgc gttatcccct gattctgtgg ataaccgtat   8700
taccgccttt gagtgagctg ataccgctcg ccgcagccga acgaccgagc gcagcgagtc   8760
agtgagcgag gaagc                                                   8775
```

<210> SEQ ID NO 8
<211> LENGTH: 5
<212> TYPE: PRT
<213> ORGANISM: Artificial
<220> FEATURE:
<223> OTHER INFORMATION: Heavy chain CDR1 region

<400> SEQUENCE: 8

Asp Tyr Asn Met Asp
1               5

<210> SEQ ID NO 9
<211> LENGTH: 17
<212> TYPE: PRT
<213> ORGANISM: Artificial
<220> FEATURE:
<223> OTHER INFORMATION: Heavy chain CDR2 region
<220> FEATURE:
<221> NAME/KEY: misc_feature
<222> LOCATION: (16)..(16)
<223> OTHER INFORMATION: Xaa is K or Q

<400> SEQUENCE: 9

Asp Ile Asn Pro Asn Tyr Asp Thr Thr Ser Tyr Asn Gln Lys Phe Xaa
1               5                   10                  15

Gly

<210> SEQ ID NO 10
<211> LENGTH: 11
<212> TYPE: PRT

-continued

```
<213> ORGANISM: Artificial
<220> FEATURE:
<223> OTHER INFORMATION: Heavy chain CDR3 region

<400> SEQUENCE: 10

Ser Met Met Gly Tyr Gly Ser Pro Met Asp Tyr
1               5                   10

<210> SEQ ID NO 11
<211> LENGTH: 15
<212> TYPE: PRT
<213> ORGANISM: Artificial
<220> FEATURE:
<223> OTHER INFORMATION: Light chain CDR1 region

<400> SEQUENCE: 11

Arg Ala Ser Lys Ser Val Ser Thr Ser Gly Tyr Ser Tyr Met His
1               5                   10                  15

<210> SEQ ID NO 12
<211> LENGTH: 7
<212> TYPE: PRT
<213> ORGANISM: Artificial
<220> FEATURE:
<223> OTHER INFORMATION: Light chain CDR2 region

<400> SEQUENCE: 12

Leu Ala Ser Asn Leu Glu Ser
1               5

<210> SEQ ID NO 13
<211> LENGTH: 9
<212> TYPE: PRT
<213> ORGANISM: Artificial
<220> FEATURE:
<223> OTHER INFORMATION: Light chain CDR3 region

<400> SEQUENCE: 13

Gln His Ile Arg Glu Leu Pro Arg Thr
1               5

<210> SEQ ID NO 14
<211> LENGTH: 4
<212> TYPE: PRT
<213> ORGANISM: Artificial
<220> FEATURE:
<223> OTHER INFORMATION: AGR2 active domain

<400> SEQUENCE: 14

Cys Pro His Ser
1

<210> SEQ ID NO 15
<211> LENGTH: 22
<212> TYPE: PRT
<213> ORGANISM: Artificial
<220> FEATURE:
<223> OTHER INFORMATION: Region necessary for the binding between AGR2
      and blocking antibody

<400> SEQUENCE: 15

Pro Leu Met Ile Ile His His Leu Asp Glu Cys Pro His Ser Gln Ala
1               5                   10                  15

Leu Lys Lys Val Phe Ala
            20
```

-continued

<210> SEQ ID NO 16
<211> LENGTH: 13
<212> TYPE: PRT
<213> ORGANISM: Artificial Sequence
<220> FEATURE:
<223> OTHER INFORMATION: heavy chain variant

<400> SEQUENCE: 16

Tyr Asn Gln Lys Phe Lys Gly Lys Ala Thr Leu Thr Val
1               5                   10

<210> SEQ ID NO 17
<211> LENGTH: 13
<212> TYPE: PRT
<213> ORGANISM: Artificial Sequence
<220> FEATURE:
<223> OTHER INFORMATION: heavy chain variant

<400> SEQUENCE: 17

Tyr Asn Gln Lys Phe Lys Gly Lys Val Thr Met Thr Val
1               5                   10

<210> SEQ ID NO 18
<211> LENGTH: 13
<212> TYPE: PRT
<213> ORGANISM: Artificial Sequence
<220> FEATURE:
<223> OTHER INFORMATION: heavy chain variant

<400> SEQUENCE: 18

Tyr Asn Gln Lys Phe Lys Gly Arg Val Thr Met Thr Val
1               5                   10

<210> SEQ ID NO 19
<211> LENGTH: 105
<212> TYPE: PRT
<213> ORGANISM: Artificial Sequence
<220> FEATURE:
<223> OTHER INFORMATION: AGR2-MBP

<400> SEQUENCE: 19

Pro Leu Met Ile Ile His His Leu Asp Glu Cys Pro His Ser Gln Ala
1               5                   10                  15

Leu Arg Arg Val Phe Ala Glu Asn Lys Glu Ile Gln Lys Leu Ala Glu
                20                  25                  30

Gln Phe Val Leu Leu Asn Leu Val Tyr Glu Thr Thr Asp Lys His Leu
            35                  40                  45

Ser Pro Asp Gly Gln Tyr Val Pro Arg Ile Met Phe Val Asp Pro Ser
        50                  55                  60

Leu Thr Val Arg Ala Asp Ile Thr Gly Arg Tyr Ser Asn Arg Leu Tyr
65                  70                  75                  80

Ala Tyr Glu Pro Ala Asp Thr Ala Leu Leu Leu Asp Asn Met Lys Lys
                85                  90                  95

Ala Leu Lys Leu Leu Lys Thr Glu Leu
            100                 105

<210> SEQ ID NO 20
<211> LENGTH: 105
<212> TYPE: PRT
<213> ORGANISM: Artificial Sequence
<220> FEATURE:
<223> OTHER INFORMATION: AGR2-MBP mutants

<400> SEQUENCE: 20

Pro Leu Met Gly Gly His Leu Asp Glu Cys Pro His Ser Gln Ala
1               5                   10                  15

Leu Arg Arg Val Phe Ala Glu Asn Lys Glu Ile Gln Lys Leu Ala Glu
            20                  25                  30

Gln Phe Val Leu Leu Asn Leu Val Tyr Glu Thr Thr Asp Lys His Leu
        35                  40                  45

Ser Pro Asp Gly Gln Tyr Val Pro Arg Ile Met Phe Val Asp Pro Ser
    50                  55                  60

Leu Thr Val Arg Ala Asp Ile Thr Gly Arg Tyr Ser Asn Arg Leu Tyr
65                  70                  75                  80

Ala Tyr Glu Pro Ala Asp Thr Ala Leu Leu Asp Asn Met Lys Lys
                85                  90                  95

Ala Leu Lys Leu Leu Lys Thr Glu Leu
            100                 105

<210> SEQ ID NO 21
<211> LENGTH: 105
<212> TYPE: PRT
<213> ORGANISM: Artificial Sequence
<220> FEATURE:
<223> OTHER INFORMATION: AGR2-MBP mutants

<400> SEQUENCE: 21

Pro Leu Met Ile Ile His Gly Gly Glu Cys Pro His Ser Gln Ala
1               5                   10                  15

Leu Arg Arg Val Phe Ala Glu Asn Lys Glu Ile Gln Lys Leu Ala Glu
            20                  25                  30

Gln Phe Val Leu Leu Asn Leu Val Tyr Glu Thr Thr Asp Lys His Leu
        35                  40                  45

Ser Pro Asp Gly Gln Tyr Val Pro Arg Ile Met Phe Val Asp Pro Ser
    50                  55                  60

Leu Thr Val Arg Ala Asp Ile Thr Gly Arg Tyr Ser Asn Arg Leu Tyr
65                  70                  75                  80

Ala Tyr Glu Pro Ala Asp Thr Ala Leu Leu Asp Asn Met Lys Lys
                85                  90                  95

Ala Leu Lys Leu Leu Lys Thr Glu Leu
            100                 105

<210> SEQ ID NO 22
<211> LENGTH: 105
<212> TYPE: PRT
<213> ORGANISM: Artificial Sequence
<220> FEATURE:
<223> OTHER INFORMATION: AGR2-MBP mutants

<400> SEQUENCE: 22

Pro Leu Met Ile Ile His His Leu Asp Glu Gly Pro His Ser Gln Ala
1               5                   10                  15

Leu Arg Arg Val Phe Ala Glu Asn Lys Glu Ile Gln Lys Leu Ala Glu
            20                  25                  30

Gln Phe Val Leu Leu Asn Leu Val Tyr Glu Thr Thr Asp Lys His Leu
        35                  40                  45

Ser Pro Asp Gly Gln Tyr Val Pro Arg Ile Met Phe Val Asp Pro Ser
    50                  55                  60

Leu Thr Val Arg Ala Asp Ile Thr Gly Arg Tyr Ser Asn Arg Leu Tyr
65                  70                  75                  80

Ala Tyr Glu Pro Ala Asp Thr Ala Leu Leu Asp Asn Met Lys Lys
                85                  90                  95

Ala Leu Lys Leu Leu Lys Thr Glu Leu
            100                 105

<210> SEQ ID NO 23
<211> LENGTH: 105
<212> TYPE: PRT
<213> ORGANISM: Artificial Sequence
<220> FEATURE:
<223> OTHER INFORMATION: AGR2-MBP mutants

<400> SEQUENCE: 23

Pro Leu Met Ile Ile His His Leu Asp Glu Cys Pro Gly Gly Gly Ala
1               5                   10                  15

Leu Arg Arg Val Phe Ala Glu Asn Lys Glu Ile Gln Lys Leu Ala Glu
            20                  25                  30

Gln Phe Val Leu Leu Asn Leu Val Tyr Glu Thr Thr Asp Lys His Leu
        35                  40                  45

Ser Pro Asp Gly Gln Tyr Val Pro Arg Ile Met Phe Val Asp Pro Ser
    50                  55                  60

Leu Thr Val Arg Ala Asp Ile Thr Gly Arg Tyr Ser Asn Arg Leu Tyr
65                  70                  75                  80

Ala Tyr Glu Pro Ala Asp Thr Ala Leu Leu Leu Asp Asn Met Lys Lys
                85                  90                  95

Ala Leu Lys Leu Leu Lys Thr Glu Leu
            100                 105

<210> SEQ ID NO 24
<211> LENGTH: 105
<212> TYPE: PRT
<213> ORGANISM: Artificial Sequence
<220> FEATURE:
<223> OTHER INFORMATION: AGR2-MBP mutants

<400> SEQUENCE: 24

Pro Leu Met Ile Ile His His Leu Asp Glu Cys Pro His Ser Gln Ala
1               5                   10                  15

Leu Gly Gly Gly Phe Ala Glu Asn Lys Glu Ile Gln Lys Leu Ala Glu
            20                  25                  30

Gln Phe Val Leu Leu Asn Leu Val Tyr Glu Thr Thr Asp Lys His Leu
        35                  40                  45

Ser Pro Asp Gly Gln Tyr Val Pro Arg Ile Met Phe Val Asp Pro Ser
    50                  55                  60

Leu Thr Val Arg Ala Asp Ile Thr Gly Arg Tyr Ser Asn Arg Leu Tyr
65                  70                  75                  80

Ala Tyr Glu Pro Ala Asp Thr Ala Leu Leu Leu Asp Asn Met Lys Lys
                85                  90                  95

Ala Leu Lys Leu Leu Lys Thr Glu Leu
            100                 105

<210> SEQ ID NO 25
<211> LENGTH: 105
<212> TYPE: PRT
<213> ORGANISM: Artificial Sequence
<220> FEATURE:
<223> OTHER INFORMATION: AGR2-MBP mutants

<400> SEQUENCE: 25

Pro Leu Met Ile Ile His His Leu Asp Glu Cys Pro His Ser Gln Ala
1               5                   10                  15

Leu Arg Arg Val Phe Ala Glu Asn Lys Glu Ile Gln Lys Leu Ala Glu
            20                  25                  30

Gln Phe Val Leu Gly Gly Val Tyr Glu Thr Thr Asp Lys His Leu
        35                  40                  45

Ser Pro Asp Gly Gln Tyr Val Pro Arg Ile Met Phe Val Asp Pro Ser
 50                  55                  60

Leu Thr Val Arg Ala Asp Ile Thr Gly Arg Tyr Ser Asn Arg Leu Tyr
 65                  70                  75                  80

Ala Tyr Glu Pro Ala Asp Thr Ala Leu Leu Leu Asp Asn Met Lys Lys
            85                  90                  95

Ala Leu Lys Leu Leu Lys Thr Glu Leu
            100                 105

<210> SEQ ID NO 26
<211> LENGTH: 105
<212> TYPE: PRT
<213> ORGANISM: Artificial Sequence
<220> FEATURE:
<223> OTHER INFORMATION: AGR2-MBP mutants

<400> SEQUENCE: 26

Pro Leu Met Ile Ile His His Leu Asp Glu Cys Pro His Ser Gln Ala
1               5                   10                  15

Leu Arg Arg Val Phe Ala Glu Asn Lys Glu Ile Gln Lys Leu Ala Glu
            20                  25                  30

Gln Phe Val Leu Leu Asn Leu Val Tyr Glu Thr Thr Asp Lys His Leu
            35                  40                  45

Ser Pro Asp Gly Gln Tyr Val Gly Gly Met Phe Val Asp Pro Ser
 50                  55                  60

Leu Thr Val Arg Ala Asp Ile Thr Gly Arg Tyr Ser Asn Arg Leu Tyr
 65                  70                  75                  80

Ala Tyr Glu Pro Ala Asp Thr Ala Leu Leu Leu Asp Asn Met Lys Lys
            85                  90                  95

Ala Leu Lys Leu Leu Lys Thr Glu Leu
            100                 105

<210> SEQ ID NO 27
<211> LENGTH: 105
<212> TYPE: PRT
<213> ORGANISM: Artificial Sequence
<220> FEATURE:
<223> OTHER INFORMATION: AGR2-MBP mutants

<400> SEQUENCE: 27

Pro Leu Met Ile Ile His His Leu Asp Glu Cys Pro His Ser Gln Ala
1               5                   10                  15

Leu Arg Arg Val Phe Ala Glu Asn Lys Glu Ile Gln Lys Leu Ala Glu
            20                  25                  30

Gln Phe Val Leu Leu Asn Leu Val Tyr Glu Thr Thr Asp Lys His Leu
            35                  40                  45

Ser Pro Asp Gly Gln Tyr Val Pro Arg Ile Met Phe Val Gly Gly Gly
 50                  55                  60

Leu Thr Val Arg Ala Asp Ile Thr Gly Arg Tyr Ser Asn Arg Leu Tyr
 65                  70                  75                  80

Ala Tyr Glu Pro Ala Asp Thr Ala Leu Leu Leu Asp Asn Met Lys Lys
            85                  90                  95

Ala Leu Lys Leu Leu Lys Thr Glu Leu
            100                 105

```
<210> SEQ ID NO 28
<211> LENGTH: 105
<212> TYPE: PRT
<213> ORGANISM: Artificial Sequence
<220> FEATURE:
<223> OTHER INFORMATION: AGR2-MBP mutants

<400> SEQUENCE: 28

Pro Leu Met Ile Ile His His Leu Asp Glu Cys Pro His Ser Gln Ala
1               5                   10                  15

Leu Arg Arg Val Phe Ala Glu Asn Lys Glu Ile Gln Lys Leu Ala Glu
            20                  25                  30

Gln Phe Val Leu Leu Asn Leu Val Tyr Glu Thr Thr Asp Lys His Leu
        35                  40                  45

Ser Pro Asp Gly Gln Tyr Val Pro Arg Ile Met Phe Val Asp Pro Ser
    50                  55                  60

Leu Thr Val Arg Ala Asp Ile Thr Gly Arg Tyr Ser Asn Arg Leu Gly
65                  70                  75                  80

Gly Gly Glu Pro Ala Asp Thr Ala Leu Leu Leu Asp Asn Met Lys Lys
                85                  90                  95

Ala Leu Lys Leu Leu Lys Thr Glu Leu
            100                 105

<210> SEQ ID NO 29
<211> LENGTH: 105
<212> TYPE: PRT
<213> ORGANISM: Artificial Sequence
<220> FEATURE:
<223> OTHER INFORMATION: AGR2-MBP mutants

<400> SEQUENCE: 29

Pro Leu Met Ile Ile His His Leu Asp Glu Cys Pro His Ser Gln Ala
1               5                   10                  15

Leu Arg Arg Val Phe Ala Glu Asn Lys Glu Ile Gln Lys Leu Ala Glu
            20                  25                  30

Gln Phe Val Leu Leu Asn Leu Val Tyr Glu Thr Thr Asp Lys His Leu
        35                  40                  45

Ser Pro Asp Gly Gln Tyr Val Pro Arg Ile Met Phe Val Asp Pro Ser
    50                  55                  60

Leu Thr Val Arg Ala Asp Ile Thr Gly Arg Tyr Ser Asn Arg Leu Tyr
65                  70                  75                  80

Ala Tyr Glu Pro Ala Asp Gly Gly Gly Leu Leu Asp Asn Met Lys Lys
                85                  90                  95

Ala Leu Lys Leu Leu Lys Thr Glu Leu
            100                 105
```